(12) United States Patent
Wrazel et al.

(10) Patent No.: US 9,328,969 B2
(45) Date of Patent: May 3, 2016

(54) HEAT EXCHANGE FLUID PURIFICATION FOR DIALYSIS SYSTEM

(71) Applicant: Outset Medical, Inc., San Jose, CA (US)

(72) Inventors: Julie Wrazel, Sunnyvale, CA (US); Gopi Lingam, Sunnyvale, CA (US); Erik Miller, Sunnyvale, CA (US); Clayton Hires, Sunnyvale, CA (US)

(73) Assignee: OUTSET MEDICAL, INC., San Jose, CA (US)

( * ) Notice: Subject to any disclaimer, the term of this patent is extended or adjusted under 35 U.S.C. 154(b) by 259 days.

(21) Appl. No.: 13/645,336

(22) Filed: Oct. 4, 2012

(65) Prior Publication Data

US 2013/0092361 A1 Apr. 18, 2013

Related U.S. Application Data

(60) Provisional application No. 61/545,084, filed on Oct. 7, 2011.

(51) Int. Cl.
| | |
|---|---|
| *A61M 1/16* | (2006.01) |
| *F28F 3/08* | (2006.01) |
| *C02F 9/00* | (2006.01) |

(Continued)

(52) U.S. Cl.
CPC ............... *F28F 3/08* (2013.01); *A61M 1/1635* (2014.02); *A61M 1/1656* (2013.01); *C02F 9/005* (2013.01); *C02F 1/001* (2013.01); *C02F 1/02* (2013.01); *C02F 1/20* (2013.01); *C02F 1/283* (2013.01); *C02F 1/441* (2013.01); *C02F 1/444* (2013.01); *C02F 2103/026* (2013.01); *C02F 2209/03* (2013.01); *C02F 2209/05* (2013.01); *C02F 2209/40* (2013.01); *C02F 2303/04* (2013.01);

(Continued)

(58) Field of Classification Search
CPC .... B01D 61/28; B01D 63/081; B01D 63/082; B01D 63/084; B01D 63/088
See application file for complete search history.

(56) References Cited

U.S. PATENT DOCUMENTS

| | | |
|---|---|---|
| 3,356,360 A | 12/1967 | Ward |
| 3,695,445 A | 10/1972 | Esmond |

(Continued)

FOREIGN PATENT DOCUMENTS

| | | |
|---|---|---|
| DE | 8702995 U1 | 5/1987 |
| EP | 0165751 A2 | 12/1985 |

(Continued)

OTHER PUBLICATIONS

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.

(Continued)

*Primary Examiner* — Allison Fitzsimmons
(74) *Attorney, Agent, or Firm* — Shay Glenn LLP

(57) ABSTRACT

Disclosed herein are small, lightweight, portable, systems that have the capability of reliably, reproducibly, highly efficiently and relatively inexpensively providing a source of purified water of sufficient volumes for home dialysis. In addition, the systems disclosed herein require much less purified water at any one time than the volumes typically needed for dialysis today, thereby further reducing the expense of running the system at home.

5 Claims, 13 Drawing Sheets

(51) Int. Cl.
- B01D 63/00 (2006.01)
- F28D 7/12 (2006.01)
- C02F 1/00 (2006.01)
- C02F 1/02 (2006.01)
- C02F 1/20 (2006.01)
- C02F 1/28 (2006.01)
- C02F 1/44 (2006.01)
- C02F 103/02 (2006.01)

(52) U.S. Cl.
CPC ............ *C02F 2303/185* (2013.01); *F28D 7/12* (2013.01); *F28F 2260/02* (2013.01); *Y02W 10/37* (2015.05)

(56) References Cited

U.S. PATENT DOCUMENTS

| | | |
|---|---|---|
| 3,710,237 A | 1/1973 | Watson et al. |
| 3,762,032 A | 10/1973 | Bowling et al. |
| 3,809,309 A | 5/1974 | Batlsta |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,172,033 A | 10/1979 | Willock |
| 4,194,014 A | 3/1980 | Hermans et al. |
| 4,204,628 A | 5/1980 | Houston et al. |
| 4,229,299 A | 10/1980 | Savitz et al. |
| 4,231,366 A | 11/1980 | Schael |
| 4,267,040 A | 5/1981 | Schal |
| 4,293,409 A | 10/1981 | Riede et al. |
| 4,310,416 A | 1/1982 | Tanaka et al. |
| 4,317,725 A | 3/1982 | Kume et al. |
| 4,342,651 A | 8/1982 | Ahrens |
| 4,476,022 A | 10/1984 | Doll |
| 4,486,303 A | 12/1984 | Brous |
| 4,500,426 A | 2/1985 | Ishii et al. |
| 4,508,622 A | 4/1985 | Polaschegg |
| 4,536,201 A | 8/1985 | Brorsson et al. |
| 4,624,784 A | 11/1986 | Lefebvre |
| 4,647,748 A | 3/1987 | Glassman |
| 4,661,246 A | 4/1987 | Ash |
| 4,689,108 A | 8/1987 | Barry, Jr. et al. |
| 4,756,835 A | 7/1988 | Wilson |
| 4,769,134 A | 9/1988 | Allan et al. |
| 4,770,787 A | 9/1988 | Heath et al. |
| 4,773,991 A | 9/1988 | Aid |
| 4,786,411 A * | 11/1988 | Benattar et al. .......... 210/321.77 |
| 4,804,474 A | 2/1989 | Blum |
| 4,827,430 A | 5/1989 | Aid et al. |
| 4,869,421 A | 9/1989 | Norris et al. |
| 4,875,619 A | 10/1989 | Anderson et al. |
| 4,889,635 A | 12/1989 | Chevallet |
| 4,894,164 A | 1/1990 | Polaschegg |
| 4,923,613 A | 5/1990 | Chevallet |
| 5,087,930 A | 2/1992 | Roy et al. |
| 5,092,836 A | 3/1992 | Polaschegg |
| 5,094,749 A | 3/1992 | Seita et al. |
| 5,147,605 A | 9/1992 | Tatsuno et al. |
| 5,232,145 A | 8/1993 | Alley et al. |
| 5,236,476 A | 8/1993 | Klick |
| 5,247,434 A | 9/1993 | Peterson et al. |
| 5,259,961 A | 11/1993 | Eigendorf |
| 5,312,550 A | 5/1994 | Hester |
| 5,313,023 A | 5/1994 | Johnson |
| 5,316,676 A | 5/1994 | Drori |
| 5,326,476 A | 7/1994 | Grogan et al. |
| 5,334,392 A | 8/1994 | Cuine et al. |
| 5,342,326 A | 8/1994 | Peppel et al. |
| 5,344,392 A | 9/1994 | Senninger et al. |
| 5,346,472 A | 9/1994 | Keshaviah et al. |
| 5,360,395 A | 11/1994 | Utterberg |
| 5,385,623 A | 1/1995 | Diaz |
| 5,394,732 A | 3/1995 | Johnson et al. |
| 5,395,351 A | 3/1995 | Munsch |
| 5,401,238 A | 3/1995 | Pirazzoli |
| 5,409,612 A | 4/1995 | Maltals et al. |
| 5,421,208 A | 6/1995 | Packard et al. |
| 5,439,451 A | 8/1995 | Collinson et al. |
| 5,469,264 A | 11/1995 | Shigemori |
| 5,472,614 A | 12/1995 | Rossi |
| 5,487,827 A | 1/1996 | Peterson et al. |
| 5,489,385 A | 2/1996 | Raabe et al. |
| 5,498,253 A | 3/1996 | Aswad et al. |
| 5,498,338 A | 3/1996 | Kruger et al. |
| 5,503,624 A | 4/1996 | Roeher et al. |
| 5,520,640 A | 5/1996 | Utterberg |
| 5,526,357 A | 6/1996 | Jandrell |
| 5,533,996 A | 7/1996 | Murphey et al. |
| 5,534,328 A | 7/1996 | Ashmead et al. |
| 5,536,258 A | 7/1996 | Folden |
| 5,571,754 A | 11/1996 | Bertin et al. |
| 5,580,460 A | 12/1996 | Polaschegg |
| 5,580,523 A | 12/1996 | Bard |
| 5,582,600 A | 12/1996 | Loh |
| 5,591,016 A | 1/1997 | Kubota et al. |
| 5,591,344 A | 1/1997 | Kenley et al. |
| 5,593,581 A | 1/1997 | Lescoche |
| 5,595,712 A | 1/1997 | Harbster et al. |
| 5,609,770 A | 3/1997 | Zimmerman et al. |
| 5,610,645 A | 3/1997 | Moore et al. |
| 5,611,214 A | 3/1997 | Wegeng et al. |
| 5,613,663 A | 3/1997 | Schmidt et al. |
| 5,615,996 A | 4/1997 | Suzuki et al. |
| 5,618,268 A | 4/1997 | Raines et al. |
| 5,618,441 A | 4/1997 | Rosa et al. |
| 5,620,433 A | 4/1997 | Aswad et al. |
| 5,620,608 A | 4/1997 | Rosa et al. |
| 5,623,969 A | 4/1997 | Raines |
| 5,624,572 A | 4/1997 | Larson et al. |
| 5,629,871 A | 5/1997 | Love et al. |
| 5,630,804 A | 5/1997 | Imada et al. |
| 5,630,935 A | 5/1997 | Treu |
| 5,643,190 A | 7/1997 | Utterberg |
| 5,645,734 A | 7/1997 | Kenley et al. |
| 5,647,984 A | 7/1997 | Hovland et al. |
| 5,648,684 A | 7/1997 | Bertin et al. |
| 5,650,071 A | 7/1997 | Brugger et al. |
| 5,662,144 A | 9/1997 | Lo et al. |
| 5,670,050 A | 9/1997 | Brose et al. |
| 5,685,835 A | 11/1997 | Brugger |
| 5,689,966 A | 11/1997 | Zess et al. |
| 5,693,008 A | 12/1997 | Brugger et al. |
| 5,697,904 A | 12/1997 | Raines et al. |
| 5,698,916 A | 12/1997 | Eguchi |
| 5,702,606 A | 12/1997 | Peter, Jr. et al. |
| 5,707,086 A | 1/1998 | Treu et al. |
| 5,711,883 A | 1/1998 | Folden et al. |
| 5,713,850 A | 2/1998 | Heilmann et al. |
| 5,716,531 A | 2/1998 | Kenley et al. |
| 5,725,773 A | 3/1998 | Polaschegg |
| 5,743,892 A | 4/1998 | Loh et al. |
| 5,744,031 A | 4/1998 | Bene |
| 5,749,226 A | 5/1998 | Bowman et al. |
| 5,769,985 A | 6/1998 | Kawakami et al. |
| 5,779,833 A | 7/1998 | Cawley et al. |
| 5,782,575 A | 7/1998 | Vincent et al. |
| 5,782,808 A | 7/1998 | Folden |
| 5,788,099 A | 8/1998 | Treu et al. |
| 5,788,851 A | 8/1998 | Kenley et al. |
| 5,792,367 A | 8/1998 | Mattisson et al. |
| 5,796,985 A | 8/1998 | O'Brien et al. |
| 5,811,062 A | 9/1998 | Wegeng et al. |
| 5,813,235 A | 9/1998 | Peterson |
| 5,817,043 A | 10/1998 | Utterberg |
| 5,851,202 A | 12/1998 | Carlsson |
| 5,858,238 A | 1/1999 | McRea et al. |
| 5,858,239 A | 1/1999 | Kenley et al. |
| 5,861,555 A | 1/1999 | Hobro et al. |
| 5,863,421 A | 1/1999 | Peter, Jr. et al. |

(56) References Cited

U.S. PATENT DOCUMENTS

| | | |
|---|---|---|
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,948,251 A | 9/1999 | Brugger |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,985,068 A | 11/1999 | Kawakami et al. |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,065,941 A | 5/2000 | Gray et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard, Jr. et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,131 B1 | 9/2001 | Hogard et al. |
| 6,284,141 B1 | 9/2001 | Shaldon et al. |
| 6,290,665 B1 | 9/2001 | Utterberg |
| 6,299,589 B1 | 10/2001 | Utterberg |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,344,139 B1 | 2/2002 | Utterberg |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,352,577 B1 | 3/2002 | Martin et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,440,095 B1 | 8/2002 | Utterberg |
| 6,454,736 B1 | 9/2002 | Ludt et al. |
| 6,454,942 B1 | 9/2002 | Shintani et al. |
| 6,464,878 B2 | 10/2002 | Utterberg |
| 6,468,056 B1 | 10/2002 | Murakoshi |
| 6,468,377 B1 | 10/2002 | Sperko et al. |
| 6,475,529 B2 | 11/2002 | Duponchelle et al. |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,490,812 B1 | 12/2002 | Bennett et al. |
| 6,503,062 B1 | 1/2003 | Gray et al. |
| 6,514,225 B1 | 2/2003 | Utterberg et al. |
| 6,514,412 B1 | 2/2003 | Insley et al. |
| 6,520,747 B2 | 2/2003 | Gray et al. |
| 6,526,357 B1 | 2/2003 | Soussan et al. |
| 6,527,728 B2 | 3/2003 | Zhang |
| 6,530,262 B1 | 3/2003 | Esser |
| 6,533,840 B2 | 3/2003 | Martin et al. |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |
| 6,595,942 B2 | 7/2003 | Kleinekofort |
| 6,595,943 B1 | 7/2003 | Burbank |
| 6,601,432 B1 | 8/2003 | Ericson et al. |
| 6,602,424 B1 | 8/2003 | Kramer et al. |
| 6,604,908 B1 | 8/2003 | Bryant et al. |

(56) References Cited

U.S. PATENT DOCUMENTS

| | | |
|---|---|---|
| 6,607,644 B1 | 8/2003 | Apffel, Jr. |
| 6,607,697 B1 | 8/2003 | Muller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,656,315 B2 | 12/2003 | Sallavanti et al. |
| 6,663,359 B2 | 12/2003 | Gray |
| 6,666,840 B1 | 12/2003 | Falkvall et al. |
| 6,666,909 B1 | 12/2003 | TeGrotenhuis et al. |
| 6,669,681 B2 | 12/2003 | Jepson et al. |
| 6,672,502 B1 | 1/2004 | Paul et al. |
| 6,673,311 B1 | 1/2004 | Sotoyama et al. |
| 6,673,314 B1 | 1/2004 | Burbank et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Donig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,709,414 B2 | 3/2004 | Weitzel et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,737,026 B1 | 5/2004 | Bergh et al. |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,403 B2 | 6/2004 | Bryant et al. |
| 6,749,814 B1 | 6/2004 | Bergh et al. |
| 6,764,460 B2 | 7/2004 | Dolecek et al. |
| 6,764,567 B2 | 7/2004 | Sperko et al. |
| 6,767,333 B1 | 7/2004 | Muller et al. |
| 6,775,577 B2 | 8/2004 | Crnkovich et al. |
| 6,793,831 B1 | 9/2004 | Paul et al. |
| 6,796,831 B1 | 9/2004 | Yasufuku et al. |
| 6,797,056 B2 | 9/2004 | David |
| 6,804,991 B2 | 10/2004 | Balschat et al. |
| 6,806,947 B1 | 10/2004 | Ekdahl et al. |
| 6,808,369 B2 | 10/2004 | Gray et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,553 B1 | 12/2004 | Burbank et al. |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | McHerron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,966,979 B2 | 11/2005 | Pedrazzi |
| 6,967,002 B1 | 11/2005 | Edgson et al. |
| 6,973,373 B2 | 12/2005 | Gray et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 6,996,951 B2 | 2/2006 | Smith et al. |
| 7,004,924 B1 | 2/2006 | Brugger et al. |
| 7,013,727 B2 | 3/2006 | Delnevo |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,083,719 B2 | 8/2006 | Bowman, Jr. et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,097,800 B2 | 8/2006 | Vigna et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,131,957 B2 | 11/2006 | Muller et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,172,569 B2 | 2/2007 | Kleinekofort |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,226,538 B2 | 6/2007 | Brugger et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,264,723 B2 | 9/2007 | Singh et al. |
| 7,279,134 B2 | 10/2007 | Chan et al. |
| 7,291,123 B2 | 11/2007 | Baraldi et al. |
| 7,300,413 B2 | 11/2007 | Burbank et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,338,460 B2 | 3/2008 | Burbank et al. |

(56) References Cited

U.S. PATENT DOCUMENTS

| | | |
|---|---|---|
| 7,347,849 B2 | 3/2008 | Brugger et al. |
| 7,351,340 B2 | 4/2008 | Connell et al. |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,410,475 B2 | 8/2008 | Krensky et al. |
| 7,421,316 B2 | 9/2008 | Gray et al. |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,501,101 B2 | 3/2009 | Wegeng et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,534,315 B1 | 5/2009 | Singh et al. |
| 7,537,687 B2 | 5/2009 | Toyoda et al. |
| 7,544,300 B2 | 6/2009 | Brugger et al. |
| 7,551,043 B2 | 6/2009 | Nguyen et al. |
| 7,559,524 B2 | 7/2009 | Gray et al. |
| 7,559,911 B2 | 7/2009 | Giannella |
| 7,575,562 B2 | 8/2009 | Oishi et al. |
| 7,575,564 B2 | 8/2009 | Childers |
| 7,588,684 B2 | 9/2009 | Brugger et al. |
| 7,591,449 B2 | 9/2009 | Raines et al. |
| 7,603,907 B2 | 10/2009 | Reiter et al. |
| 7,615,035 B2 | 11/2009 | Peppel |
| 7,618,405 B2 | 11/2009 | Young |
| 7,618,531 B2 | 11/2009 | Sugioka et al. |
| 7,621,983 B2 | 11/2009 | Neri |
| 7,622,043 B2 | 11/2009 | Sawada et al. |
| 7,632,470 B2 | 12/2009 | Tabata et al. |
| 7,641,626 B2 | 1/2010 | Tonelli et al. |
| 7,647,834 B2 | 1/2010 | O'Mahony et al. |
| 7,648,474 B2 | 1/2010 | Paolini et al. |
| 7,648,476 B2 | 1/2010 | Bock et al. |
| 7,648,477 B2 | 1/2010 | Vinci et al. |
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |
| 7,699,992 B2 | 4/2010 | Sternby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,176 B2 | 6/2010 | Tonelli et al. |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,766,301 B2 | 8/2010 | Gray et al. |
| 7,771,379 B2 | 8/2010 | Treu |
| 7,771,380 B2 | 8/2010 | Jonsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,785,284 B2 | 8/2010 | Baraldi et al. |
| 7,788,038 B2 | 8/2010 | Oshita et al. |
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Sternby |
| 7,824,354 B2 | 11/2010 | Vinci et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jonsson et al. |
| 8,293,114 B2 | 10/2012 | Jonsson et al. |
| 8,298,427 B2 | 10/2012 | Ficheux et al. |
| 8,323,503 B2 | 12/2012 | Levin et al. |
| 8,343,085 B2 | 1/2013 | Toyoda et al. |
| 8,394,046 B2 | 3/2013 | Nuernberger et al. |
| 8,419,933 B2 | 4/2013 | Rohde et al. |
| 8,419,945 B2 | 4/2013 | Browning et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,603,020 B2 | 12/2013 | Roger et al. |
| 8,608,658 B2 | 12/2013 | Burbank et al. |
| 8,617,393 B2 | 12/2013 | Remkes et al. |
| 8,641,615 B2 | 2/2014 | Burbank et al. |
| 8,647,290 B2 | 2/2014 | Masala et al. |
| 8,679,348 B2 | 3/2014 | Burbank et al. |
| 2002/0023879 A1 | 2/2002 | Hadden |
| 2002/0045265 A1 | 4/2002 | Bergh et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0156991 A1 | 8/2003 | Halas et al. |
| 2003/0163077 A1 | 8/2003 | Kim et al. |
| 2003/0168590 A1 | 9/2003 | Weiss et al. |
| 2003/0183345 A1 | 10/2003 | Soberay |
| 2003/0209475 A1 | 11/2003 | Connell et al. |
| 2003/0217972 A1 | 11/2003 | Connell et al. |
| 2003/0220598 A1 | 11/2003 | Busby et al. |
| 2003/0221777 A1 | 12/2003 | McHerron et al. |
| 2003/0222022 A1 | 12/2003 | Connell et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0019313 A1 | 1/2004 | Childers et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0064080 A1 | 4/2004 | Cruz et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0084372 A1 | 5/2004 | Connell et al. |

(56) References Cited

U.S. PATENT DOCUMENTS

| | | |
|---|---|---|
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0011833 A1 | 1/2005 | Stahl |
| 2005/0061740 A1 | 3/2005 | Felding et al. |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0085760 A1 | 4/2005 | Ware et al. |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2005/0220681 A1 | 10/2005 | Chang et al. |
| 2006/0079698 A1 | 4/2006 | Joshi et al. |
| 2006/0113250 A1 | 6/2006 | Krensky et al. |
| 2006/0157413 A1 | 7/2006 | Bene et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0158249 A1 | 7/2007 | Ash |
| 2007/0158268 A1 | 7/2007 | DeComo |
| 2007/0184576 A1 | 8/2007 | Chang et al. |
| 2007/0215644 A1 | 9/2007 | Otis et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0093298 A1* | 4/2008 | Browning et al. ............ 210/646 |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0245017 A1 | 10/2009 | Paul et al. |
| 2009/0306573 A1 | 12/2009 | Gagner et al. |
| 2009/0309835 A1 | 12/2009 | Levin et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0321046 A1 | 12/2010 | Randall et al. |
| 2010/0326914 A1 | 12/2010 | Drost et al. |
| 2010/0326916 A1 | 12/2010 | Wrazel et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132838 A1 | 6/2011 | Curtis et al. |
| 2011/0132841 A1 | 6/2011 | Rohde et al. |
| 2011/0189048 A1 | 8/2011 | Curtis et al. |
| 2011/0192796 A1 | 8/2011 | Smejtek et al. |
| 2011/0295175 A1 | 12/2011 | Felder et al. |
| 2011/0300230 A1 | 12/2011 | Peterson et al. |
| 2012/0029937 A1 | 2/2012 | Neftel et al. |
| 2012/0103902 A1 | 5/2012 | Childers et al. |
| 2012/0205312 A1 | 8/2012 | Hogard |
| 2012/0211422 A1 | 8/2012 | Thys |
| 2012/0248039 A1 | 10/2012 | Rohde et al. |
| 2012/0292246 A1 | 11/2012 | Jovanovic et al. |
| 2012/0298580 A1 | 11/2012 | Gronau et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0030344 A1 | 1/2013 | Gronau et al. |
| 2013/0037485 A1 | 2/2013 | Wilt et al. |
| 2013/0056418 A1 | 3/2013 | Kopperschmidt et al. |
| 2013/0146541 A1 | 6/2013 | Weigel et al. |
| 2013/0180339 A1 | 7/2013 | Brugger |
| 2013/0186829 A1 | 7/2013 | Callan et al. |
| 2013/0206693 A2 | 8/2013 | Thys |
| 2013/0213890 A1 | 8/2013 | Kelly et al. |
| 2013/0267883 A1 | 10/2013 | Medrano |
| 2013/0270185 A1 | 10/2013 | Kreymann |
| 2014/0014580 A1 | 1/2014 | Ritter |
| 2014/0018727 A1 | 1/2014 | Burbank et al. |
| 2014/0069861 A1 | 3/2014 | Browning et al. |
| 2014/0072288 A1 | 3/2014 | Newell |
| 2014/0076058 A1 | 3/2014 | Brugger et al. |
| 2014/0299545 A1 | 10/2014 | Wrazel et al. |
| 2014/0319035 A1 | 10/2014 | Burbank et al. |
| 2015/0005699 A1 | 1/2015 | Burbank et al. |
| 2015/0204733 A1 | 7/2015 | Newell et al. |

FOREIGN PATENT DOCUMENTS

| | | |
|---|---|---|
| EP | 0 324 922 A2 | 7/1989 |
| EP | 0547025 A1 | 6/1993 |
| EP | 0679100 A0 | 11/1995 |
| EP | 0796997 A1 | 9/1997 |
| EP | 2246079 A1 | 11/2010 |
| EP | 2497507 B1 | 9/2012 |
| EP | 2535070 A1 | 12/2012 |
| GB | 1 289 738 A | 9/1972 |
| JP | 59-58002 | 4/1984 |
| JP | S60143803 A | 7/1985 |
| JP | 2002143298 A | 5/2002 |
| JP | 55-14045 | 6/2014 |
| WO | WO-00/16916 A1 | 3/2000 |
| WO | WO-02/40874 A1 | 5/2002 |
| WO | WO-02/076529 A1 | 10/2002 |
| WO | WO03/076661 A1 | 9/2003 |
| WO | WO-2005/045894 A2 | 5/2005 |
| WO | WO2006/039293 A2 | 4/2006 |
| WO | WO-2006/042079 A1 | 4/2006 |
| WO | WO-2007/023328 A1 | 3/2007 |
| WO | WO2007/089855 A2 | 8/2007 |
| WO | WO-2007/126360 A1 | 11/2007 |
| WO | WO2008/027967 A1 | 3/2008 |
| WO | WO-2008/106191 A2 | 9/2008 |
| WO | WO-2010/006137 A1 | 1/2010 |
| WO | WO-2010/024963 A1 | 3/2010 |
| WO | WO-2010/027435 A1 | 3/2010 |
| WO | WO-2010/040824 A1 | 4/2010 |
| WO | WO-2010/062698 A2 | 6/2010 |
| WO | WO2010/085764 | 7/2010 |
| WO | WO-2010/151419 A1 | 12/2010 |
| WO | WO-2011/156279 A1 | 12/2011 |

OTHER PUBLICATIONS

Anglés et al., "Plasticized starch/Tunicin Whiskers Nanocomposite Materials. 2. Mechanical behavior," Macromolecules, 34, pp. 2921-2931, Mar. 2001.

California Energy Commission; Development of Supported Polymeric Liquid Membrane Technology for Aqueous MTBE Mitigation,

(56) References Cited

OTHER PUBLICATIONS

EPRI, Palo Alto, CA, California Energy Commission, Sacramento, CA: Doc. No. 1006577; 70 pgs.; Jul. 2002.
Demura et al., "Ductile Thin Foil of Ni3Al," Mechanical Properties of Structural Films, ASTM International Nov. 2000 Symposium (Orlando, FL), pp. 248-261, published Oct. 1, 2001.
Favier et al.; Nanocomposite materials from latex and cellulose whiskers; Polymers for Advanced Technologies; 6; pp. 351-355; Jan. 1995.
Federal Energy Technology Center, "Technology Development Through Industrial Partnerships," (Tech. Dev. Data Sheet), 12 pgs., Sep. 1998.
Grunert et al., "Progress in the Development of Cellulose Reinforced Nanocomposites," PMSE Preprints 2000, 82, 232, 2 pgs., Mar. 2000.
Haas, "Further development of MMW and SMMW platelet feed horn arrays," Astron. Soc. Pac. Conf. Ser., vol. 75, pp. 99-105, Multi-Feed Systems for Radio Telescopes, Workshop held in Tucson, Arizona, May 16-18, 1994.
Koeneman et al., "Feasibility of Micro Power Supplies for MEMS," (pre-publication copy) J. MicroElectoMechanical Sys., 6(4), pp. 355-362, Dec. 1997.
Morin et al., "Nanocomposites of Chitin Whiskers from Riftia Tubes and Poly (caprolactone)," Macromolecules, vol. 35, pp. 2190-2199, Feb. 2002.
Stroock et al., "Chaotic Mixer for Microchannels," Science, 295, pp. 647-651, Jan. 2002.
Thorsen et al.; Microfluidic Large-Scale Integration; Science; 298; pp. 580-584; Oct. 18, 2002.
Wegeng et al., "Chemical system miniaturization," Proceedings of the AIChE Spring National Meeting, pp. 1-13, Feb. 1996.
Hogard et al.; U.S. Appl. No. 14/699,875 entitled "Dialysis System and Methods" filed Apr. 29, 2015.
Peterson et al.; U.S. Appl. No. 14/808,827 entitled "Fluid Purification System," filed Jul. 24, 2015.
Miller; U.S. Appl. No. 14/827,054 entitled "Through-Plate Microchannel Membrane Devices," filed Aug. 14, 2015.
Hogard et al.; U.S. Appl. No. 14/821,283 entitled "Dialysis system and methods," filed Aug. 7, 2015.
Hogard et al.; U.S. Appl. No. 14/821,307 entitled "Dialysis system and methods," filed Aug. 7, 2015.
Hogard et al.; U.S. Appl. No. 14/821,325 entitled "Dialysis system and methods," filed Aug. 7, 2015.
Hogard et al.; U.S. Appl. No. 14/821,349 entitled "Dialysis system and methods," filed Aug. 7, 2015.
Hogard et al.; U.S. Appl. No. 14/821,362 entitled "Dialysis system and methods," filed Aug. 7, 2015.
Miller et al.; U.S. Appl. No. 14/858,876 entitled "Dialysis machine having a conductivity sensor for determining fluid properties," filed Sep. 18, 2015.
German Patent Fulltext file with English machine translation for publication No. DE8702995, published May 7, 1987.
Nakamura et al., "Research on Pressure Welding Conditions of Various Work Metals (Effects of Contact Pressure, Surface Expansion Ratio and Temperature)," JSME International Journal, Series III 31(3), 612-617, Sep. 1988.
Nakao et al., "Diffusion Bonding of Intermetallic Compound TiAl," ISIJ International, 31(10), 1260-1266, Oct. 1991.
Oddy et al., "Electrokinetic Instability Micromixing," Anal. Chem., 73(24), pp. 5822-5832, Dec. 2001.
Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.
Paillet et al., "Chitin Whisker Reinforced Thermoplastic Nanocomposites," Macromolecules, vol. 34, No. 19, pp. 6527-6530, Sep. 2001.
Paul et al., "Microlamination for Microtechnology-based Energy, Chemical, and Biological Systems," ASME IMECE, ASE vol. 39, pp. 45-52, Nashville, Tennessee, Nov. 15-20, 1999.
Pluess, "Application of Controlled Thermal Expansion in Diffusion Bonding for the High-Volume Microlamination of MECS Devices," Thesis (MS), Oregon State University, 193 pgs., Sep. 2004.
Porter et al.; Cost drivers in microlamination based on a high volume production system design; ASME 2002 Conf. Proc.; New Orleans, Louisiana; pp. 267-274; Nov. 17-22, 2002.
Sharma et al., "The Application of Surface Mount Technology to Multi-Scale Process Intensification," ASPE, pp. 1-4, Oct. 2003.

\* cited by examiner

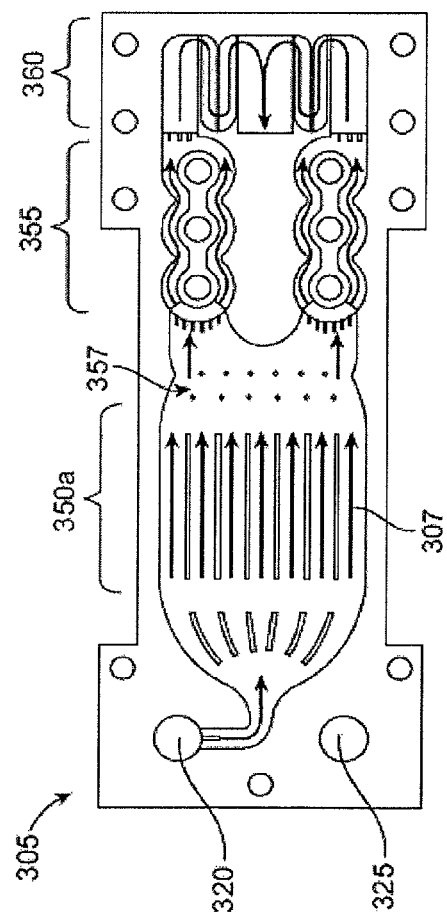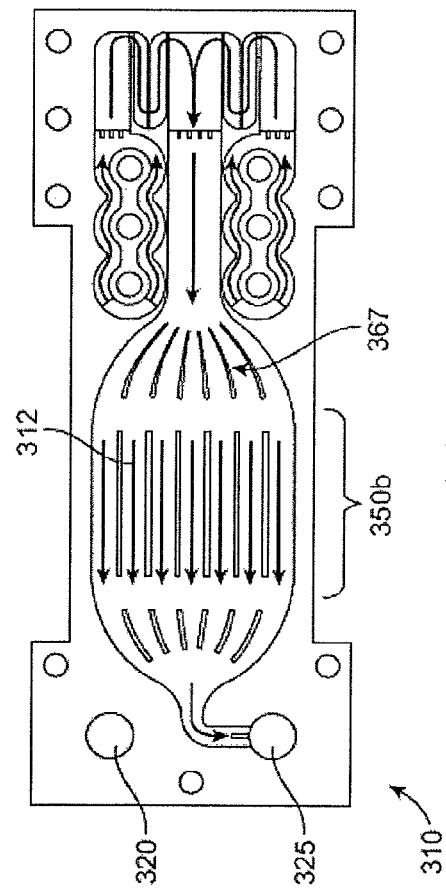
FIG. 7A
FIG. 7B

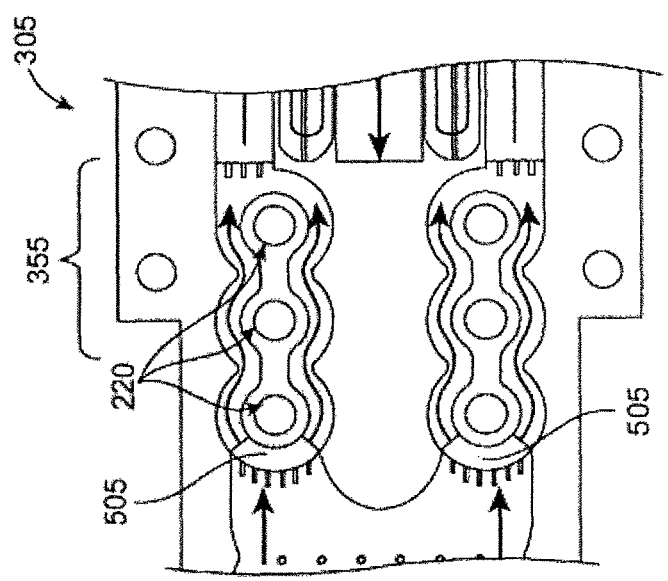

US 9,328,969 B2

HEAT EXCHANGE FLUID PURIFICATION FOR DIALYSIS SYSTEM

REFERENCE TO RELATED APPLICATIONS

This application claims the benefit of priority of U.S. Provisional Patent Application Ser. No. 61/545,084, entitled "Heat Exchange Fluid Purification For Dialysis System," and filed Oct. 7, 2011. Priority of the aforementioned filing date is hereby claimed and the disclosures of the aforementioned patent application is hereby incorporated by reference in its entirety.

This application is related to the following U.S. Patent Applications: (1) U.S. patent application Ser. No. 12/795,371, entitled "Microfluidic Devices" and filed Jun. 7, 2010, which claims priority to U.S. Provisional Patent Application Ser. No. 61/220,117, filed on Jun. 24, 2009; (2) U.S. patent application Ser. No. 12/795,498, entitled "Dialysis System With Ultrafiltration Control" and filed Jun. 7, 2010, which claims priority to U.S. Provisional Patent Application Ser. No. 61/267,043, filed on Dec. 5, 2009; (3) U.S. patent application Ser. No. 12/795,382, entitled "Fluid Purification System" and filed Jun. 7, 2010; and (4) U.S. patent application Ser. No. 12/795,444, entitled "Dialysis System" and filed Jun. 7, 2010. This application is also related to International Patent Application No. PCT/US2010/037621, entitled "Microfluidic Devices," and filed Jun. 7, 2010. The disclosures of the aforementioned patent applications are hereby incorporated by reference in their entirety.

BACKGROUND

The present disclosure concerns a dialysis system, such as a microfluidic or flow field dialyzer capable of being fluidly coupled to a dialysate stream and a blood stream, and a method for using the dialysis system.

There are, at present, hundreds of thousands of patients in the United States with end-stage renal disease. Most of those require dialysis to survive. United States Renal Data System projects the number of patients in the U.S. on dialysis will climb past 600,000 by 2012. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Given the demanding nature of in-center dialysis, many patients have turned to home dialysis as an option. Home dialysis provides the patient with scheduling flexibility as it permits the patient to choose treatment times to fit other activities, such as going to work or caring for a family member. Unfortunately, current dialysis systems are generally unsuitable for use in a patient's home. One reason for this is that current systems are too large and bulky to fit within a typical home. Current dialysis systems are also energy-inefficient in that they use large amounts of energy and require enormous amounts of water for proper use. Although some home dialysis systems are available, they generally use complex flow-balancing technology that is relatively expensive to manufacture and most systems are designed with a system of solenoid valves that create high noise levels. As a result, most dialysis treatments are performed at dialysis centers.

SUMMARY

In view of the foregoing, there is a need for improved fluid purification systems, particularly water purification systems for preparing fluids for use in conjunction with home dialysis.

In one aspect, disclosed is a water treatment device, including at least first and second laminae arranged in a stacked relationship so as to form a stack of laminae, each lamina having a fluid flow field, the fluid flow field of the first lamina configured for receiving blood and the fluid flow field of the second lamina configured for receiving dialysate; a first cut-out in the first lamina, wherein the first cut-out surrounds at least a portion of the fluid flow field of the first lamina; a second cut-out on the second lamina, wherein the second cut-out surrounds at least a portion of the fluid flow field of the second lamina, and wherein the first and second cut-outs vertically align with one another in the stack to form a collective cut-out that extends through the stack; and a first plate on the top of the stack and a second plate on the bottom of the stack, wherein the first and second plates enclose the top and bottom of the collective cut-out creating an insulating chamber to the fluid flow fields of the stack.

Each cut-out can surround a respective flow field along at least three sides of the flow field. Each cut-out surrounds at least eighty percent of the respective flow field. The stack can include more than two laminae. The collective cut-out can form a U-shape around the fluid flow fields of the stack. The device can further include at least one heat transfer layer interleaved between the first and second flow fields, across which layer dialysis of the blood occurs when in operation. The insulating channel can inhibit loss of heat from one or more regions of the flow field. A partial vacuum can be formed within the insulating chamber. The fluid flow fields of the laminae can have a coiled configuration and be surrounded by a coiled insulating chamber.

Other features and advantages should be apparent from the following description of various embodiments, which illustrate, by way of example, the principles of the disclosed devices and methods.

BRIEF DESCRIPTION OF THE DRAWINGS

FIG. 7A shows an exemplary embodiment of an inlet lamina that forms at least one inlet pathway where fluid flows in an inward direction through the heat exchange system.

FIG. 7B shows an exemplary embodiment of an outlet lamina that forms at least one outlet pathway where fluid flows in an outward direction through the heat exchange system.

FIG. 8 shows an enlarged view of a heater region of the inlet lamina.

DETAILED DESCRIPTION

Disclosed herein are small, lightweight, portable, systems that have the capability of reliably, reproducibly, highly efficiently and relatively inexpensively providing a source of purified water of sufficient volumes for home dialysis. In addition, the systems disclosed herein require much less purified water at any one time than the volumes typically needed for dialysis today, thereby further reducing the expense of running the system at home. In addition, the systems described herein are capable of producing real-time, on-demand ultrapure water for dialysis, the gold standard of present-day dialysis. Disclosed herein are in-line, non-batch water purification systems that use a microfluidics heat exchanger for heating, purifying and cooling water. The systems described herein consume relatively low amounts of energy. The systems described herein although suitable for use in a home dialysis system, can be used in other environments where water purification is desired. The systems can also be used to purify fluids other than water. As will be described in more detail below, the systems described herein can be connected to a residential source of water (such as a running water tap to provide a continuous or semi-continuous household stream of water) and can produce real-time pasteurized water for use in home dialysis, without the need to heat and cool large, batched quantities of water.

Dialysis System

Figure 1:
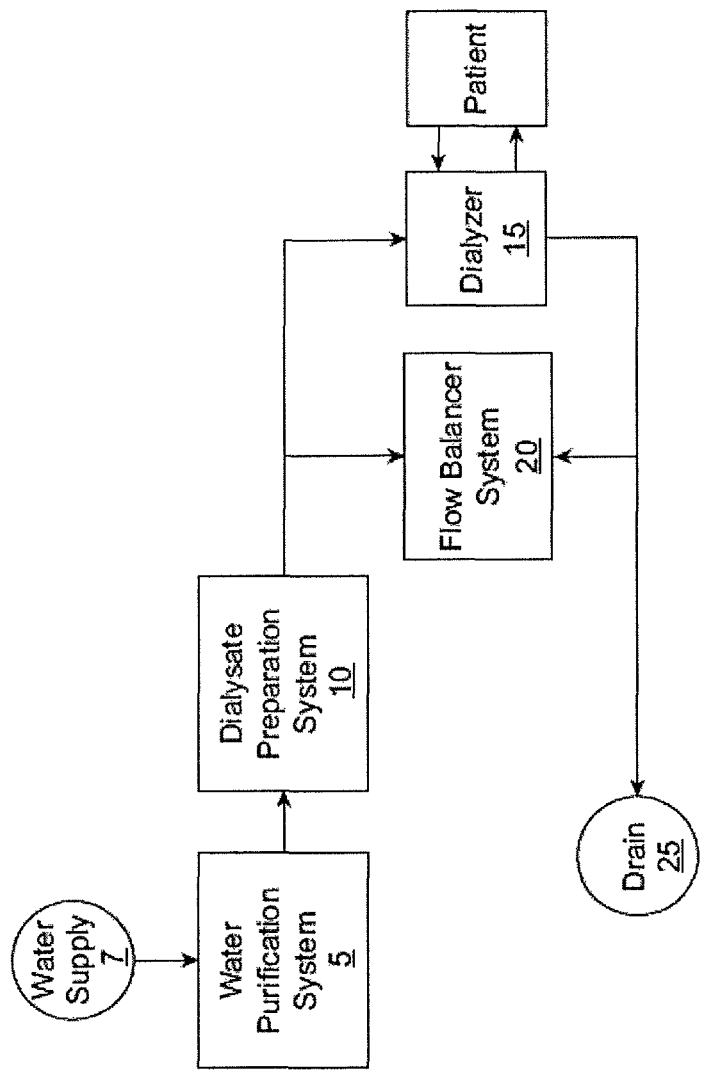
FIG. 1 shows a high level, schematic view of an implementation of a dialysis system.

FIG. 1 shows a high level, schematic view of an implementation of a dialysis system. The dialysis system can include a plurality of subsystems that collectively operate to receive and purify water, use the water to prepare dialysate, and supply the dialysate to a dialyzer that performs various types of dialysis on the blood of a patient such as hemodialysis, ultrafiltration and hemodiafiltration. The dialysis system can include plumbing that provides fluid pathways for water, dialysis, and blood to flow through the dialysis system, as well as one or more pumps that interface with the plumbing for driving fluid flow through the system. The dialysis system can also include one or more sensors, such as fluid flow sensors, pressure sensors, conductivity sensors, etc. for sensing and reporting one or more characteristics of fluid flowing through the system.

In an embodiment, the entire dialysis system (including the water preparation and purification system, dialysate preparation system, flow balancer system, dialyzer, and hardware, such as plumbing and sensors) is contained within a single housing that is compact and portable. In addition, the dialysis system can prepare dialysate using a tap water, such as in a home or hotel room. In an embodiment, the entire dialysis system consumes less than about 22" by 14" by 9" of space when dry, which generally corresponds to the size limit for carry-on baggage of an airline. In an embodiment, the entire dialysis system weighs less than about fifty pounds when dry.

With reference still to FIG. 1, the dialysis system can include a water preparation and purification system 5 that purifies water from a water supply 7. The water purification system 5 can supply the purified water to a dialysate preparation system 10 that uses the purified water to prepare dialysate. The dialysis system can further include a dialyzer 15 that receives the dialysate from the dialysate preparation system 10 and performs dialysis on a patient's blood. In an embodiment, the dialyzer 15 and the dialysate preparation system 10 both can interface with a flow balancer system 20 that regulates the flow of dialysate to the dialyzer to achieve different types of dialysis, including hemodialysis, ultrafiltration, and hemodiafiltration, as described in detail below.

Diffusion is the principal mechanism in which hemodialysis removes waste products such as urea, creatinine, phosphate and uric acid, among others, from the blood. A differential between the chemical composition of the dialysate and the chemical composition of the blood within the dialyzer causes the waste products to diffuse through a membrane from the blood into the dialysate. Ultrafiltration is a process in dialysis where fluid is caused to move across the membrane from the blood into the dialysate, typically for the purpose of removing excess fluid from the patient's blood stream. Along with water, some solutes are also drawn across the membrane via convection rather than diffusion. Ultrafiltration is a result of a pressure differential between a blood compartment and a dialysate compartment in the dialyzer where fluid moves from a higher pressure to a lower pressure. In some circumstances, by design or unintentional consequence, fluid in the dialysate compartment is higher than the blood compartment causing fluid to move from the dialysate compartment into the blood compartment. This is commonly referred to as reverse ultrafiltration.

In hemodiafiltration, a high level of ultrafiltration is created, greater than the amount required to remove fluid from the patient's blood, for the purpose of increasing convective solute transport across the membrane. The amount of fluid in excess of what is required to be removed from the patient's blood must therefore be returned to the blood stream in order to avoid an adverse hemodynamic reaction. This is accomplished by intentionally increasing the pressure in the dialysate compartment of the dialyzer to cause the appropriate amount of reverse ultrafiltration. This process of ultrafiltration alternating with reverse ultrafiltration is often referred to as "push-pull hemodiafiltration." This is a significant improvement over more common methods of hemodiafiltration where sterile fluid is administered to the patient in a location outside of the dialyzer.

In use, the patient is coupled to the dialyzer 15 such that the patient's blood flows into and out of the dialyzer 15 using devices and techniques known to those skilled in the art. The dialysis system prepares dialysate using water from a household water source, such as a tap, that has been previously prepared through filtration and purification before being mixed with various dialysate components to make the dialysate, and then flows the dialysate through the dialyzer in communication with the blood such that one or more of the dialysis processes on the blood is performed. The water purification system includes a plurality of subsystems that collectively operate to purify the water including pasteurization of the water, as described more fully below. The purified water is then mixed with dialysate concentrates to form dialysate, which is supplied to the dialyzer 15 and to the flow balancer system, which regulates the flow of dialysate to the dialyzer 15 to selectively achieve different types of dialysis, including hemodialysis, ultrafiltration, and hemodiafiltration, as described more fully below. The dialysis system supplies the used dialysate to a drain 25. In an embodiment, the system recaptures heat from the used dialysate before going to the drain.

Subsystems of Dialysis System

Embodiments of the various subsystems of the dialysis system are now described, including the water purification system 5, dialysate preparation system 10, dialyzer 15, and flow balancer system 20. It should be appreciated that the descriptions are examples of implementations and that variations are possible.

A. Water Purification Sub-system

Figure 2:
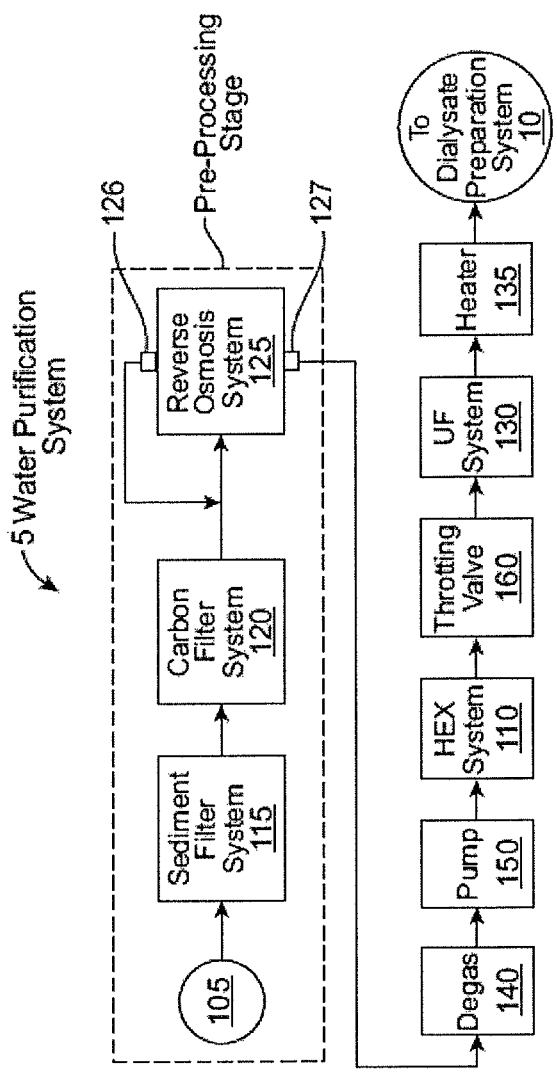
FIG. 2 shows a high level, schematic view of an implementation of a water purification system of the dialysis system.

FIG. 2 shows a high level, schematic view of the water purification system 5. The water purification system 5 includes a plurality of subsystems and/or components each of which is schematically represented in FIG. 2. Although it is described in the context of purifying water, the water purification system 5 can be used to purify fluids other than water. Water enters the fluid purification system at an entry location 105 (from the water supply 7 in FIG. 1) and communicates with each of the subsystems and components as the water flows along a flow pathway toward the dialysate preparation system 10. The subsystems may include, for example, a sediment filter system 115, a carbon filter system 120, a reverse osmosis system 125, an ultrafilter system 130, an auxiliary heater system 135, a degassifier system 140, or any combination thereof.

Upon exiting the fluid purification system 5, and prior to entering the dialysate preparation system 10, the fluid is in a purified state. This preferably includes the fluid being in a pasteurized state although the fluid system does not necessarily pasteurize the fluid in all circumstances. The embodiment shown in FIG. 2 is exemplary and not all of the components shown in FIG. 2 are necessarily included in the water purification system 5. The individual components included in the system may vary depending on the type and level of purification or pasteurization required. The quantity and sequential order of the subsystems along the flow pathway shown in FIG. 2 is for purposes of example and it should be appreciated that variations are possible.

A method for purifying water using the fluid purification system 5 is now described including a description of a fluid flow path through the system. As mentioned, water can enter the water purification system 5 via an entry location 105. The entry location may include a three-way valve that may be set such that incoming water is received from one of at least two water sources. One such water source may be household water tap. Alternately, the valve may be set to receive recirculated water that was previously routed through the water purification system 5 and that is re-routed back into the system such as to flush the system. When the valve is set to receive recirculated water, the re-circulated water may bypass one or more of the subsystems as it flows through the water purification system 5.

When the valve is set to receive water from the household water tap, the incoming water can first flow through at least one sediment filter system 115, which includes one or more sediment filters that filter sediment from the water flowing therethrough. In an embodiment, the sediment filter 115 removes particulate matter down to 5 microns or even 1 micron. A pressure sensor may be positioned upstream of the sediment filter(s) and a pressure sensor may also be positioned downstream of the sediment filter(s) in order to monitor flow conditions. In addition, the flow pathway may include one or more pressure regulators configured to regulate fluid pressure to achieve a desired flow rate through the system. The pressure regulator(s) may be used to compensate for a household tap having a flow rate that is above or below a desired range.

The water can then flow through a carbon filter system 120, which can include one or more carbon filters that filter materials such as organic chemicals, chlorine and chloramines from the water. In an embodiment, the carbon filter system 120 includes two carbon filters with a sample port positioned in the flow path between the carbon filters. The sample port provides an operator with access to the water flowing through the system, such as for quality control purposes. In an embodiment, at least one pressure sensor and at least one conductivity sensor are positioned in the flow pathway downstream of the carbon filter system 120. The conductivity sensor provides an indication as to the percentage of dissolved solids removed from the water. In addition, one or more pumps may be positioned at various locations along the water flow pathway such as between the filter subsystems.

The water can flow from the carbon filter system 120 to a reverse osmosis system 125 configured to remove particles from the water pursuant a reverse osmosis procedure. The reverse osmosis system 125 can remove greater than 95% of the total dissolved solids from the water. The reverse osmosis system 125 may have two outlets including a waste water outlet 126 and a pure water outlet 127. The waste water outlet 126 outputs waste water from the reverse osmosis system 125. The waste water can be rerouted back into an upstream location of the water pathway for re-entry into the reverse osmosis system 125. In this regard, a sensor such as a conductivity sensor may be located upstream of the reverse osmosis system 125 as a means of verifying the contents of the water. Alternately, the waste water outlet 126 may supply the waste water to a drain.

The sediment filter system 115, carbon filter system 120, and reverse osmosis system 125 collectively form a pre-processing stage that removes a majority of dissolved solids, bacteria contamination, and chemical contamination, if any, from the water. The water is therefore in a somewhat macro-purified state as it exits the pre-processing stage. Thus, the preprocessing stage supplies relatively clean water to the downstream pump(s) and also to a downstream heat exchange system 110 that pasteurizes the water. The preprocessing stage can reduce or eliminate the potential for scale build-up and corrosion during heating of the water by the heat exchange system 110.

One or more degassifier systems 140 may be positioned in the flow pathway upstream and/or downstream of the heat exchange system 110 for removing entrained gas from the water. The degassifier system 140 may include any of a variety of components adapted to remove entrained gas from the water. For example, the degassifier systems 140 may include a spray chamber and/or a bubble trap.

After the water passes the pre-processing stage, the water can flow through a pump 150 that pumps the water into the heat exchange (HEX) system 110. The heat exchange system 110 can heat the water to a temperature that achieves pasteurization of the water. In an embodiment, the heat exchange system 110 is a microfluidic heat exchange system. Embodiments of microfluidic heat exchange systems are described in detail in U.S. patent application Ser. No. 12/795,382, filed Jun. 7, 2010, and U.S. Patent Application Publication No. 2010/0326916, filed Jun. 7, 2010, which are each incorporated by reference in their entireties.

The pump 150 may be used to increase the water pressure to a level higher than the saturation pressure encountered in the heat exchange system 110. This prevents phase change of the water inside the heat exchange system 110. Thus, if the highest temperature reached in the heat exchange system 110 is 150 degrees Celsius where the water would have a saturation pressure known to one of skill in the art, the pressure of the water coming out of the pump would exceed that saturation pressure by a certain safety margin, such as 10 psi, to ensure that no phase change occurs. The pump can increase the water pressure to a level that is at or exceeds the saturation pressure to ensure no localized boiling. This can be important where the heat exchange system is used to pasteurize water and the water is exposed to high temperatures that may be greater than 138 degrees Celsius, i.e., well above the boiling point of water at atmospheric pressure.

After leaving the heat exchange system 110, the water can pass into a throttling valve 160, such as flow restrictor, which maintains the pressure though the water path from the pump 150 to outlet of the heat exchange system 110. The throttling valve 160 and the pump 150 may be controlled and adjusted to achieve a flow rate and a desired pressure configuration. The pump 150 and the throttling valve 160 may communicate with one another in a closed loop system to ensure the required pressure is maintained for the desired flow rate and temperature. One or more temperature sensors and/or flow sensors may be positioned along the flow pathway downstream of the heat exchange system for use in controlling the pump 150 and the throttling valve 160.

After the water leaves the throttling valve 160, it can pass to an ultrafilter (UF) system 130 that removes macromolecules and all or substantially all of the dead bacteria killed by the pasteurization process from the water to ensure no endotoxins remain in the water before mixing the dialysate. The presence of macromolecules may be detrimental to the dialysis process. The water can then pass through a heater system 135 that may, if necessary or desired, heat the water to a desired temperature, such as to normal body temperature (98.6 degrees Fahrenheit). From the heater system 135, the water can pass to the dialysate preparation system 10.

In an embodiment, a second heat exchange system is positioned in the flow pathway upstream of the heater system 135. The second heat exchange system can be used to further cool the water that comes out of the heat exchange system 110 in the event that the water is above a predetermined desired temperature, such as 37 degrees Celsius. The second heat exchange system may be connected to a separate source of cool water that will then act as a cooling agent or it can be connected to the water rejected from the reverse osmosis system 125. The second heat exchange system may be used in environments where the water source produces very warm water and/or when the heat exchange system 110 is unable to cool the water sufficiently for use in dialysis.

B. Microfluidic Heat Exchanger

Figure 3:
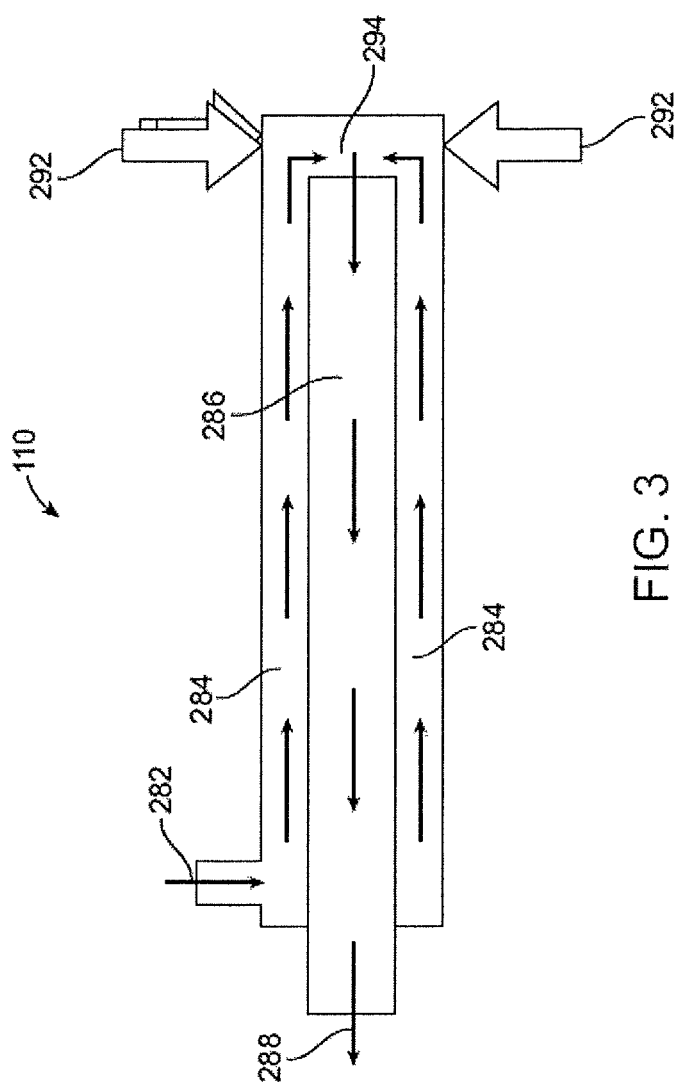
FIG. 3 shows a schematic, plan view of an implementation of a microfluidic heat exchange system adapted to heat and cool a single fluid without the use of a second fluid stream to add heat to or remove heat from the fluid.

As discussed above, the water purification system 5 may employ a heat exchange system 110 that is adapted to pasteurize the water. FIG. 3 shows a schematic, plan view of an embodiment of the microfluidic heat exchange system 110, which is configured to achieve pasteurization of a liquid (such as water) flowing through the microfluidic heat exchange system without the need for a second fluid stream to add heat to or remove heat from the liquid. FIG. 3 is schematic and it should be appreciated that variations in the actual configuration of the flow pathway, such as size and shape of the flow pathway, are possible. Embodiments of microfluidic heat exchange systems are described in detail in U.S. patent application Ser. No. 12/795,382, filed Jun. 7, 2010, and U.S. Patent Application Publication No. 2010/0326916, filed Jun. 7, 2010, which are each incorporated by reference in their entireties.

As described more fully below, the microfluidic heat exchange system defines a fluid flow pathway that can include (1) at least one fluid inlet; (2) a heater region where incoming fluid is heated to a pasteurization temperature via at least one heater; (3) a residence chamber where fluid remains at or above the pasteurization temperature for a predetermined time period; (4) a heat exchange section where incoming fluid receives heat from hotter (relative to the incoming fluid) outgoing fluid, and the outgoing fluid cools as it transfers heat to the incoming fluid; and (5) a fluid outlet where outgoing fluid exits in a cooled, pasteurized state. Depending on the desired temperature of the outgoing fluid, one or more additional heat exchanges may be used downstream to adjust the actual temperature of the outgoing fluid to the desired temperature for use, for example, in dialysis. This is especially true in warmer climates, where incoming water may be tens of degrees higher than water supplied in colder climates, which will result in higher outlet temperatures than may be desired unless further cooling is applied.

In an embodiment, the flow pathway is at least partially formed of one or more microchannels, although using microfluidic flow fields as disclosed below for portions of the fluid flow pathway such as the heat exchange section is also within the scope of the invention. The relatively reduced dimensions of a microchannel enhance heat transfer rates of the heat exchange system by providing a reduced diffusional path length and amount of material between counterflow pathways in the system. In an embodiment, a microchannel has at least one dimension less than about 1000 µm. The dimensions of a microchannel can vary and are generally engineered to achieve desired heat transfer characteristics. A microchannel in the range of about 0.1 to about 1 mm in hydraulic diameter generally achieves laminar fluid flow through the microchannel, particularly in a heat exchange region of the microchannel. The small size of a microchannel also permits the heat exchange system 110 to be compact and lightweight. In an embodiment, the microchannels are formed in one or more laminae that are arranged in a stacked configuration.

The flow pathway of the microfluidic heat exchange system 110 may be arranged in a counterflow pathway configuration. The flow pathway can be arranged such that cooler, incoming fluid flows in thermal communication with hotter, outgoing fluid. The hotter, outgoing fluid transfers thermal energy to the colder, incoming fluid to assist the heaters in heating the incoming fluid to the pasteurization temperature. This internal preheating of the incoming fluid to a temperature higher than its temperature at the inlet reduces the amount of energy used by the heaters to reach the desired peak temperature. In addition, the transfer of thermal energy from the outgoing fluid to the incoming fluid causes the previously heated, outgoing fluid to cool prior to exiting through the fluid outlet. Thus, the fluid is "cold" as it enters the microfluidic heat exchange system 110, is then heated (first via heat exchange and then via the heaters) as it passes through the internal fluid pathway, and is "cold" once again as it exits the microfluidic heat exchange system 110. The fluid can enter the microfluidic heat exchange system 110 at a first temperature and is heated (via heat exchange and via the heaters) to a second temperature that is greater than the first temperature. As the fluid follows an exit pathway, the fluid (at the second temperature) transfers heat to incoming fluid such that the fluid drops to a third temperature that is lower than the second temperature and that is higher than the first temperature.

Exemplary embodiments of a fluid pathway and corresponding components of the microfluidic heat exchange system 110 are now described in more detail with reference to FIG. 3, which depicts a bayonet-style heat exchanger, with the inlet and outlet on one side of the device, a central heat exchange portion, and a heating section toward the opposite end. The fluid can enter the microfluidic heat exchange system 110 through an inlet 282. In the illustrated embodiment, the flow pathway can branch into one or more inflow microchannels 284 that are positioned in a counterflow arrangement with an outflow microchannel 286. As mentioned, the microfluidic heat exchange system 110 may be formed by a stack of layered laminae. The inflow microchannels 284 may be positioned in separate layers with respect to the outflow microchannels 286 such that inflow microchannels 284 are positioned above or below the outflow microchannels 286 in an interleaved fashion. In another embodiment, the inflow microchannels 284 and outflow microchannels 286 are positioned on a single layer.

The outflow microchannel 286 can communicate with an outlet 288. In the illustrated embodiment, the inlet 282 and outlet 288 are positioned on the same end of the microfluidic heat exchange system 110, although the inlet 282 and outlet 288 may also be positioned at different positions relative to one another. The counterflow arrangement places the inflow microchannels 284 in thermal communication with the outflow microchannel 286. In this regard, fluid in the inflow microchannels 284 may flow along a directional vector that is oriented about 180 degrees to a directional vector of fluid flow in the outflow microchannels 286. The inflow and outflow microchannels may also be in a cross flow configuration wherein fluid in the inflow microchannels 284 may flow along a directional vector that is oriented between about 180 degrees to about 90 degrees relative to a directional vector of fluid flow in the outflow microchannels 286. The orientation of the inflow microchannels relative to the outflow microchannels may vary in any matter that is configured to achieve the desired degree of thermal communication between the inflow and outflow microchannels.

One or more heaters 292 can be positioned in thermal communication with at least the inflow microchannels 284 such that the heaters 292 can provide heat to fluid flowing in the system. The heaters 292 may be positioned inside the inflow microchannels 284 such that fluid must flow around multiple sides of the heaters 292. Or, the heaters 292 may be positioned to the side of the inflow microchannels 284 such that fluid flows along one side of the heaters 292. In any event, the heaters 292 can transfer heat to the fluid sufficient to cause the temperature of the fluid to achieve a desired temperature, which may include a pasteurization temperature in the case of water to be purified. In an embodiment, the fluid is water and the heaters 292 assist in heating the fluid to a temperature of at least 100 degrees Celsius at standard atmospheric pressure. In an embodiment, the fluid is water and the heaters 292 assist in heating the fluid to a temperature of at least 120 degrees Celsius. In an embodiment, the fluid is water and the heaters 292 assist in heating the fluid to a temperature of at least 130 degrees Celsius. In an embodiment, the fluid is water and the heaters 292 assist in heating the fluid to a temperature of at least 138 degrees Celsius. In another embodiment, the fluid is water and is heated to a temperature in the range of about 138 degrees Celsius to about 150 degrees Celsius. In another embodiment, the fluid is heated to the highest temperature possible without achieving vaporization of the fluid.

Thus, the microfluidic heat exchange system 110 may maintain the fluid as a single phase liquid. Because water typically changes phases from a liquid into a gaseous state around 100 degrees Celsius, the heat exchange system can be pressurized such that the heating water at the temperatures set forth above are maintained at single-phase liquid throughout. Pressures above the saturation pressure corresponding to the highest temperature in the heat exchange system are sufficient to maintain the fluid in a liquid state. As a margin of safety, the pressure can be kept at 10 psi or higher above the saturation pressure. In an embodiment, the pressure of water in the microfluidic heat exchange system is maintained greater than 485 kPa to prevent boiling of the water, and may be maintained significantly in excess of that level, such as 620 kPa or even as high as 900 kPa, in order to ensure no boiling occurs. These pressures can be maintained in the heat exchange system using a pump and a throttling valve. A pump upstream of the heat exchange system and a throttling valve downstream of the heat exchange system can be used where the pump and throttling valve operate in a closed loop control setup (such as with sensors) to maintain the desired pressure and flow rate throughout the heat exchange system.

Once the fluid has been heated to the pasteurization temperature, the fluid can pass into a residence chamber 294 where the fluid remains heated at or above the pasteurization temperature for a predetermined amount of time, referred to as the "residence time", or sometimes referred to as the "dwell time". In an embodiment, the dwell time can be less than or equal to one second, between one and two seconds, or at least about two seconds depending on the flow path length and flow rate of the fluid. Higher temperatures are more effective at killing bacteria and shorter residence times mean a more compact device. Ultrahigh temperature pasteurization, that is designed to kill all Colony Forming Units (CFUs) of microbiological organisms of 0.1 CFU/ml down to a concentration of less than $10^{-6}$ CFU/ml (such as for purifying the water for use with infusible dialysate), is defined to be achieved when water is heated to a temperature of 138 degrees Celsius to 150 degrees Celsius for a dwell time of at least about two seconds. Ultrapure dialysate has a bacterial load no greater than 0.1 CFU/ml. Table 1 (shown in the attached figures) indicates the required temperature and residence time to achieve various levels of pasteurization. The heat exchange system described herein is configured to achieve the various levels of pasteurization shown in Table 1.

The fluid can then flow from the residence chamber 294 to the outflow microchannel 286, where it flows toward the fluid outlet 288. As mentioned, the outflow microchannel 286 can be positioned in a counterflow relationship with the inflow microchannel 284 and in thermal communication with the inflow microchannel 284. In this manner, outgoing fluid (flowing through the outflow microchannel 286) thermally communicates with the incoming fluid (flowing through the inflow microchannel 284). As the heated fluid flows through the outflow microchannel 286, thermal energy from the heated fluid transfers to the cooler fluid flowing through the adjacent inflow microchannel 284. The exchange of thermal energy results in cooling of the fluid from its residence chamber temperature as it flows through the outflow microchannel 286. Moreover, the incoming fluid is preheated via the heat exchange as it flows through the inflow microchannel 284 prior to reaching the heaters 292. In an embodiment, the fluid in the outflow microchannel 284 is cooled to a temperature that is no lower than the lowest possible temperature that precludes bacterial infestation of the fluid. When the heat exchange system pasteurizes the fluid, bacteria in the fluid down to the desired level of purification are dead as the fluid exits the heat exchange system. In such a case, the temperature of the fluid after exiting the heat exchange system may be maintained at room temperature before use in dialysis. In another embodiment, the fluid exiting the heat exchange system is cooled to a temperature at or below normal body temperature.

Although an embodiment is shown in FIG. 3 as having an outlet channel sandwiched between an inflow channel, other arrangements of the channels are possible to achieve the desired degrees of heating and cooling and energy requirements of the heaters. Common to all embodiments, however, is that all fluid pathways within the system are designed to be traveled by a single fluid, without the need for a second fluid to add heat to or remove heat from the single fluid. In other words, the single fluid relies on itself, at various positions in the fluid pathway, to heat and cool itself.

The dimensions of the microfluidic heat exchange system 110 may vary. In an embodiment, the microfluidic heat exchange system 110 is sufficiently small to be held in the hand of a user. In another embodiment, the microfluidic heat exchange system 110 is a single body that weighs less than 5 pounds when dry. In another embodiment, the microfluidic heat exchange portion 350 of the overall system 110 has a volume of about one cubic inch. The dimensions of the microfluidic heat exchange system 110 may be selected to achieve desired temperature and dwell time characteristics.

As mentioned, an embodiment of the microfluidic heat exchange system 110 is made up of multiple laminar units stacked atop one another to form layers of laminae. A desired microfluidic fluid flow path may be etched into the surface of each lamina such that, when the laminae are stacked atop one another, microfluidic channels or flow fields are formed between the lamina. Furthermore, both blind etching and through etching may be used for forming the channels in the laminae. In particular, through etching allows the fluid to change the plane of laminae and move to other layers of the stack of laminae. This occurs in one embodiment at the outlet of the inflow laminae where the fluid enters the heater section, as described below. Through etching allows all laminae around the heater section to participate in heating of the fluid instead of maintaining the fluid only in the plane of the inlet laminae. This embodiment provides more surface area and lower overall fluid velocity to facilitate the heating of the fluid to the required temperature and ultimately contributes to the efficiency of the device.

The microchannels or flow fields derived from blind and/or through etching of the laminae form the fluid flow pathways. The microchannels and flow fields described herein can be at least partially formed of one or more microfluidic flow fields as disclosed in U.S. patent application Ser. No. 12/795,382, filed Jun. 7, 2010, and U.S. Patent Application Publication No. 2010/0326916, filed Jun. 7, 2010, which are both incorporated herein by reference in their entireties.

FIG. 7A shows a plan view of an embodiment of an inlet lamina 305 that forms at least one inlet pathway where fluid flows in an inward direction (as represented by arrows 307) through the heat exchange system 110. FIG. 7B shows a plan view an embodiment of an outlet lamina 310 that forms at least one outlet pathway where fluid flows in an outward direction (as represented by arrows 312) through the heat exchange system 110. The inlet pathway and the outlet pathway may each include one or more microchannels. In some embodiments, the inlet and outlet pathway include a plurality of microchannels arranged in parallel relationship.

Figure 7C:
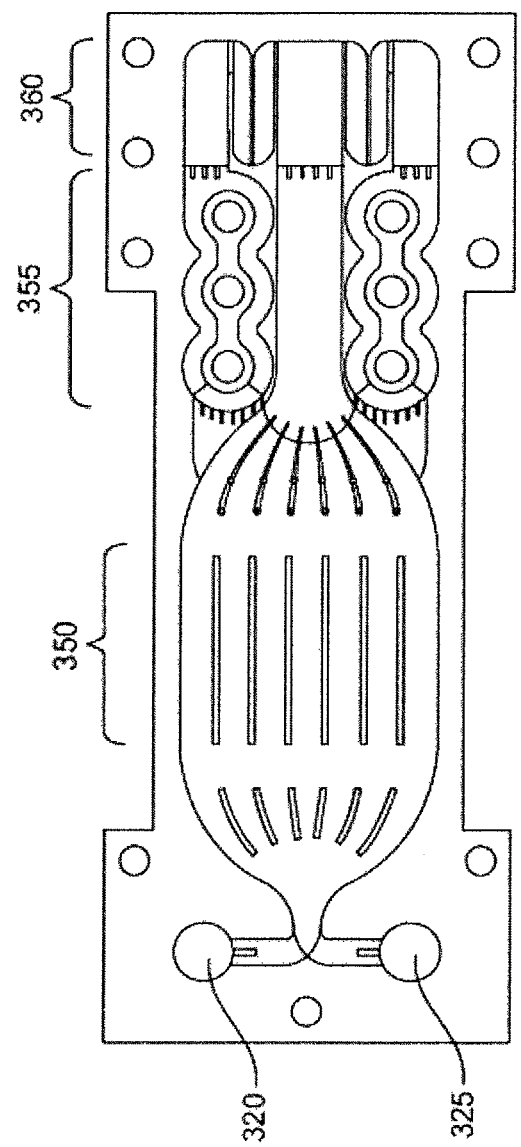
FIG. 7C shows an exemplary embodiment having superimposed inlet and outlet laminae.

FIGS. 7A and 7B show the laminae 305 and 310 positioned adjacent to each other, although in assembled device the laminae are stacked atop one another in an interleaved configuration. FIG. 7C shows the inlet lamina 305 and outlet lamina 310 superimposed over one another showing both the inlet pathway and outlet pathway. The inlet lamina 305 and outlet lamina 310 can be stacked atop one another with a fluid conduit therebetween so fluid may flow through the conduit from the inlet pathway to the outlet pathway, as described more fully below. When stacked, a transfer layer may be interposed between the inlet lamina 305 and the outlet lamina 310. The transfer layer is configured to permit heat to transfer from fluid in the outlet pathway to fluid in the inlet pathway. The transfer layer may be any material capable of conducting heat from one fluid to another fluid at a sufficient rate for the desired application. Relevant factors include, without limitation, the thermal conductivity of the heat transfer layer 110, the thickness of the heat transfer layer, and the desired rate of heat transfer. Suitable materials include, without limitation, metal, metal alloy, ceramic, polymer, or composites thereof. Suitable metals include, without limitation, stainless steel, iron, copper, aluminum, nickel, titanium, gold, silver, or tin, and alloys of these metals. Copper may be a particularly desirable material. In another embodiment, there is no transfer layer between the inlet and outlet laminae and the laminae themselves serve as the thermal transfer layer between the flow pathways.

The inlet lamina 305 and outlet lamina 310 both include at least one inlet opening 320 and at least one outlet opening 325. When the inlet lamina 305 and outlet lamina 310 are stacked atop one another and properly aligned, the inlet openings 320 align to collectively form a fluid pathway that extends through the stack and communicates with the inlet pathway of the inlet lamina 305, as shown in FIG. 7C. Likewise, the outlet openings 325 also align to collectively form a fluid pathway that communicates with the outlet pathway of the outlet laminae 310. Any quantity of inlet laminae and outlet laminae can be stacked to form multiple layers of inlet and outlet pathways for the heat exchange system 110. The quantity of layers can be selected to provide predetermined characteristics to the microfluidic heat exchange system 110, such as to vary the amount of heat exchange in the fluid, the flow rate of the fluid capable of being handled by the system, etc. In an embodiment, the heat exchange system 110 achieves incoming liquid flow rates of at least 100 ml/min.

With reference again to FIG. 7A, the inlet pathway and outlet pathway each include a heat exchange region. The heat exchange regions are referred to collectively using the reference numeral 350 and individually using reference numeral 350a (for the inlet pathway) and reference numeral 350b (for the outlet pathway). The heat exchange regions 350 are the locations where the colder fluid (relative to the fluid in the outlet pathway) of the inlet pathway receives heat transferred from the hotter fluid (relative to the fluid in the inlet pathway) of the outlet pathway. As discussed above, the relatively colder fluid in the inflow pathway is positioned to flow in thermal communication with the relatively hotter fluid in the outflow pathway. In this layered embodiment, the inflow pathway is positioned immediately above (or below) the outflow pathway when the lamina are stacked. Heat transfers across the transfer layer from the fluid in the outflow pathway to the fluid in the inflow pathway as a result of the temperature differential between the fluid in the inflow pathway and the fluid in the outflow pathway and the thermal conductivity of the material separating the two pathways. Again rather than including a series of microchannels, the heat exchange regions may also include a microfluidic flow field as described above.

With reference still to FIG. 7A, the fluid in the inflow pathway flows into a heater region 355 from the heat exchange region 350. A plurality of pins 357 may be positioned in the inlet flow pathway between the heat exchange region 350 and the heater region 355 (see also FIG. 8). The pins 357 disrupt the fluid flow and promote mixing, which may improve both fluid flow and heat distribution. In an embodiment, the inflow pathway bifurcates into at least two flow pathways in the heater region 355 to accommodate a desired flow rate. Alternatively only one flow path through the heater region may be utilized, or three or more flow paths may be selected. The heater region 355 includes one or more heaters 220 that thermally communicate with fluid flowing through this region, but are hermetically isolated from the flow path. The heaters 220 add heat to the incoming fluid sufficient to raise temperature of the fluid to the desired temperature, which may include a pasteurization temperature. The incoming fluid was previously preheated as it flowed through the heat exchange region 350. This advantageously reduced the energy requirements for the heaters. The heater region 355 serves as both a region where the heater 220 heats the fluid and as a residence chamber where the fluid remains heated at or above the desired temperature for a predetermined amount of time. The fluid flow path can completely encircle each of the heaters 220 so that any shim material conducting heat away from the heater 220 can have fluid flowing over it to receive the heat, thereby minimizing heat loss to the environment. In addition, the flowpaths around each heater 220 can be relatively narrow so that non-uniform heating due to separation from the heaters 220 will be avoided.

The laminae in the stack may include through-etches at entry locations 505 to the heater region 355 such that fluid entering the heater region 355 can pass through all the laminae in the stack. Through-etching allows all laminae around the heater region 355 to participate in heating of the fluid instead of maintaining the fluid only in the plane of the inlet laminae. This provides more surface area between the fluid and the heaters 220 and also provides lower overall fluid velocity to facilitate the heating of the fluid to the required temperature.

As mentioned, the inflow pathway may bifurcate into multiple flow pathways. Each pathway may include one or more heaters 220 arranged within the pathway so as to maximize or otherwise increase the amount of surface area contact between the heaters 220 and fluid flowing through the pathways. In this regard, the heaters 220 may be positioned towards the middle of the pathway such that the fluid must flow around either side of the heaters 220 along a semicircular or otherwise curvilinear pathway around the heaters 220. The heaters 220 can vary in configuration. In an embodiment, the heaters 220 are conventional cartridge heaters with a ⅛-inch diameter which can be run in an embodiment at a combined rate of between about 70,000 and 110,000 W/m$^2$, which results in energy usages of less than 100 W in one embodiment, and less than 200 W in another embodiment, for the entire stack running at about 100 mL/minute. In an embodiment, the system uses six heaters in a configuration of three heaters per flow pathway wherein each heater uses about 70 W for a 100 ml/min flow rate. In an embodiment the fluid is forced to flow around the heaters in paths 1.6 mm wide. The heaters 220 can include a 150-Watt McMaster-Carr cartridge heater (model 3618K451).

With reference again to FIG. 7A, the inflow pathway transitions from the heater section 355 to the residence chamber 360. By the time the fluid flows into the residence chamber 360, it has been heated to the desired temperature, such as the pasteurization temperature, as a result of the heat transfer in the heat exchange region 350 and/or by being heated in the heater section 355. In the case of multiple laminae being stacked, the residence chamber 360 may be a single chamber that spans all of the layers of laminae in the stack such that the fluid from each inlet lamina flows into a single volume of fluid in the residence chamber 360. The residence chamber 360 is configured such that fluid flow 'shortcuts' are eliminated, all of the fluid is forced to travel a flow pathway such that no portion of the fluid will reside in the residence chamber 360 for the less than the desired duration at a specified flow rate, and the fluid is maintained at or above the pasteurization temperature for the duration of the time (i.e., the dwell time) that the fluid is within the residence chamber 360. In effect, the residence time is a result of the dimensions of the flowpath through the residence area and the flow rate. It will thus be apparent to one of skill in the art how to design a residence pathway for a desired duration.

With reference again to FIG. 7B, the outlet pathway passes between the heaters 220, which act as insulators for the fluid to lessen the likelihood of the fluid losing heat at this stage of the flow pathway. The heated fluid of the outlet pathway then flows toward the heat exchange region 350$b$. The outlet flow pathway expands prior to reaching the heat exchange region 350$b$. A set of expansion fans 367 directs the fluid into the expanded heat exchange region 350$b$ of the outlet pathway, where the fluid thermally communicates with the cooler fluid in the inflow pathway. As discussed, heat from the fluid in the hotter outflow pathway transfers to the cooler fluid in the inflow pathway. This results in cooling of the outflowing fluid and heating of the inflowing fluid. The fluid then flows from the heat exchange region 350$b$ to the outlet opening 325. At this stage, the fluid is in a cooled, pasteurized state.

The width of the ribs separating channels in the heat exchange portion can be reduced, which would have the effect of increasing the available heat transfer area and reducing the length of the heat exchange portion required for the desired energy efficiency level of the device. Energy efficiency levels of at least about 85%, and in some embodiment of at least about 90% can be achieved, meaning that 90% of the thermal energy from the outgoing fluid can be transferred to the incoming fluid stream and recaptured without loss.

As mentioned, the microfluidic heat exchange system 110 may be formed of a plurality of lamina stacked atop one another and diffusion bonded. Additional information concerning diffusion bonding is provided by U.S. Patent Application Publication nos. 2008/0108122 and 2009/0092526, which are incorporated herein by reference. In an embodiment, the stack includes multiple sets of lamina with each set including an inlet lamina 305 juxtaposed with an outlet lamina 310. Each set of juxtaposed inlet lamina and outlet lamina forms a single heat exchange unit. The stack of lamina may therefore include a plurality of heat exchange units wherein each unit is formed of an inlet lamina 305 coupled to an outlet lamina 310. The flow pathways for each lamina may be formed by etching on the surface of the lamina, such as by etching on one side only of each lamina. When the laminae are juxtaposed, the etched side of a lamina seals against the un-etched sided of an adjacent, neighboring lamina. This may provide desirable conditions for heat exchange and separation of the incoming fluid (which is not pasteurized) and the outgoing fluid (which is pasteurized).

Figure 9:
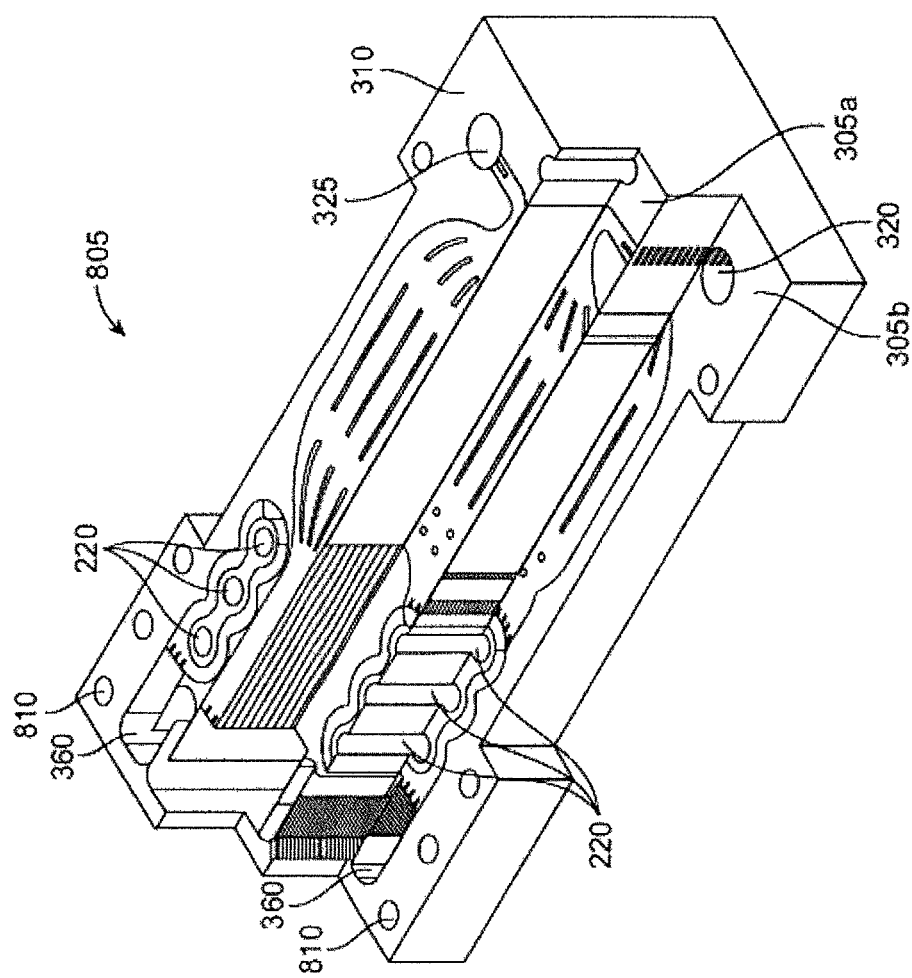
FIG. 9 shows a perspective view of an exemplary stack 805 of laminae.

FIG. 9 shows a perspective view of a stack 805 of laminae. The stack 805 is shown in partial cross-section at various levels of the stack including at an upper-most outlet lamina 310, a mid-level inlet lamina 305$a$, and a lower level inlet lamina 305$b$. As mentioned, the stack 805 is formed of alternating inlet laminae and outlet laminae interleaved with one another. The heaters 220 are positioned within cut-outs that extend through the entire stack 805 across all the laminae in the stack 805. The residence chamber 360 and the aligned inlet openings 320 and outlet openings 325 also extend entirely through the stack 805. The laminae may also include one or more holes 810 that align when the lamina are stacked to form shafts through which alignment posts may be inserted. The laminae are stacked in a manner that achieves proper alignment of the laminae. For example, when properly stacked, the inlet openings 320 of all the laminae align to collectively form an inlet passage for fluid to flow into the system and the outlet openings 325 align to collectively form an outlet passage, as shown in FIG. 9. The properly-aligned stack of laminae may also include one or more seats for coupling the heaters 220 in the stack. One or more features can be used to assist in proper alignment of the laminae in the stack, such as alignment posts and/or visual indicators of proper alignment. The stack may include a top cover positioned on the top-most lamina and a bottom cover positioned on the bottom-most lamina.

Dialysis systems known in the art can be relatively energy-inefficient and require large amounts of energy for proper use limiting their use in home dialysis. The heat exchange system 110 described herein can have an insulating architecture that prevents heat loss of the water passing therethrough such as to the outside environment. As such, the overall power consumption is reduced or minimized and the systems are optimized for use in home dialysis.

Figure 10:
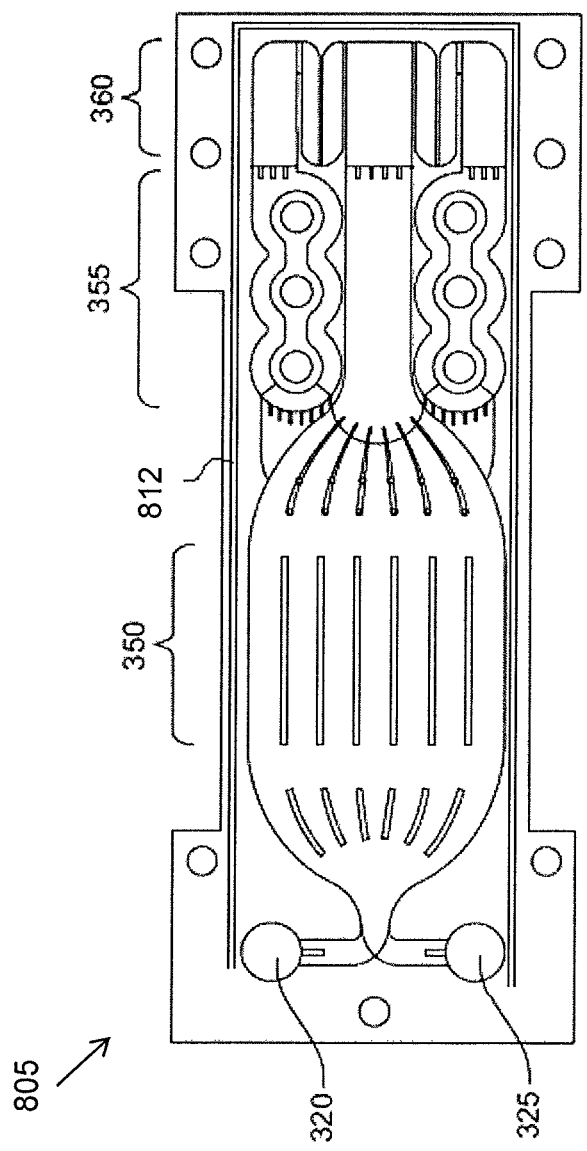
FIG. 10 shows a plan view of another embodiment of superimposed laminae stack having an insulating architecture.

In some embodiments, the stack 805 of laminae of the heat exchange system 110 includes an external insulation wrap. The stack 850 can also be encased in insulation to prevent heat loss to the outside environment. In other embodiments, the stack 805 can include one or more insulating channels 812 that can prevent or inhibit loss of heat from one or more regions of the flow field. As shown in FIG. 10, the insulating channel 812 can be formed by one or more cut-outs that each extend through a respective laminae in the stack. The cut-outs can be positioned such that they vertically align with one another when the laminae are properly stacked atop one another. In this manner, the cut-outs collectively form a chamber that extends through and across all of the laminae in the stack. In some embodiments, the method of forming the stack resulting in the laminae adhering to each other may result in the formation of a partial vacuum in the channel 812. The vacuum can enhance the insulating properties of the channel 812. The chamber serves as an insulator that prevents or inhibits heat loss from the fluid pathway. In the regard, the chamber can be sized and shaped to extend around the entire perimeter of or a portion of the perimeter of the fluid pathway. For example, the channel can extend along at least 4, 3, 2 or 1 side of the flow path. In various embodiments, the channel extends around 50, 60, 70, 80, 90, or 95 percent of a perimeter of the flow pathway.

Figure 11:
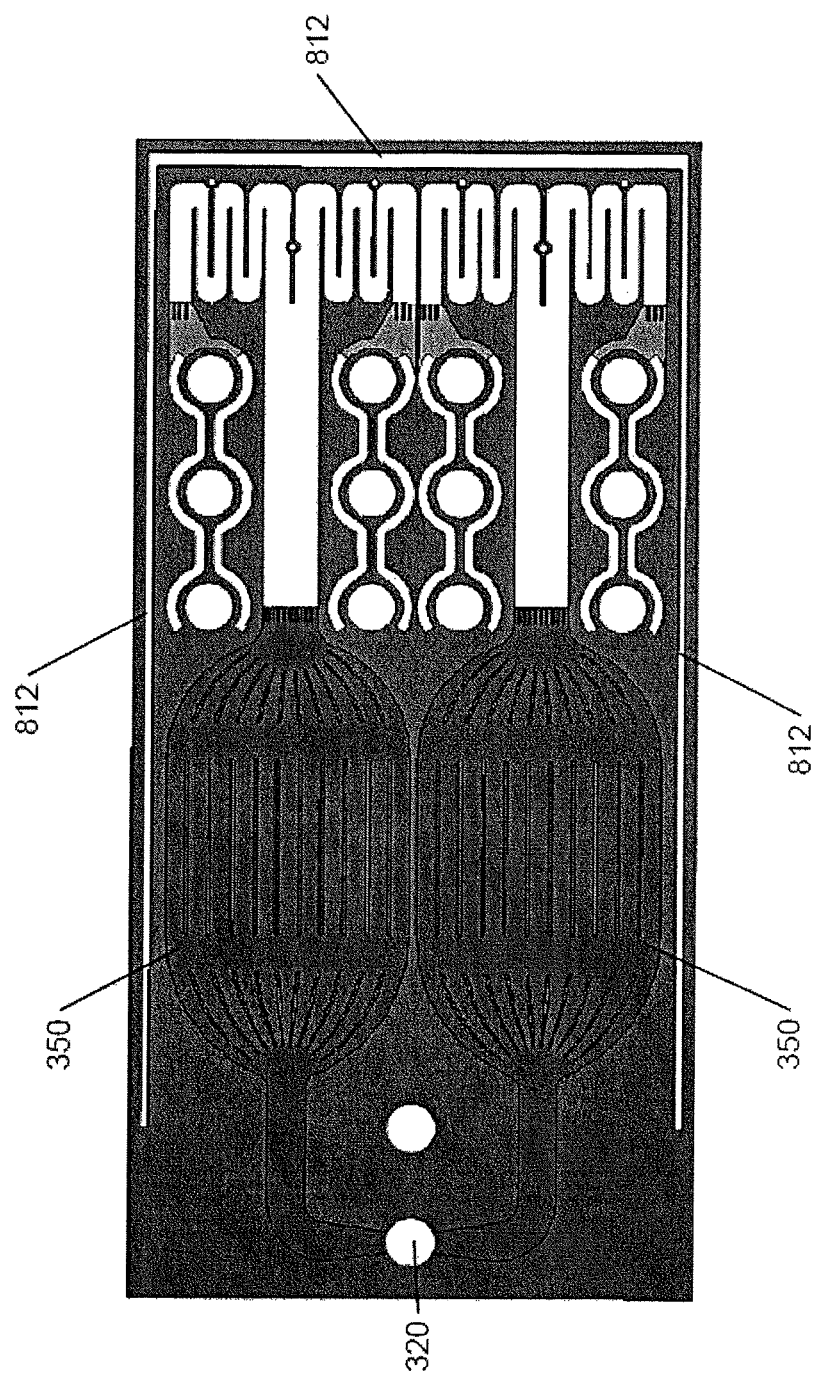
FIG. 11 shows an embodiment of a lamina having a pair of heat exchange regions.
Figure 12:
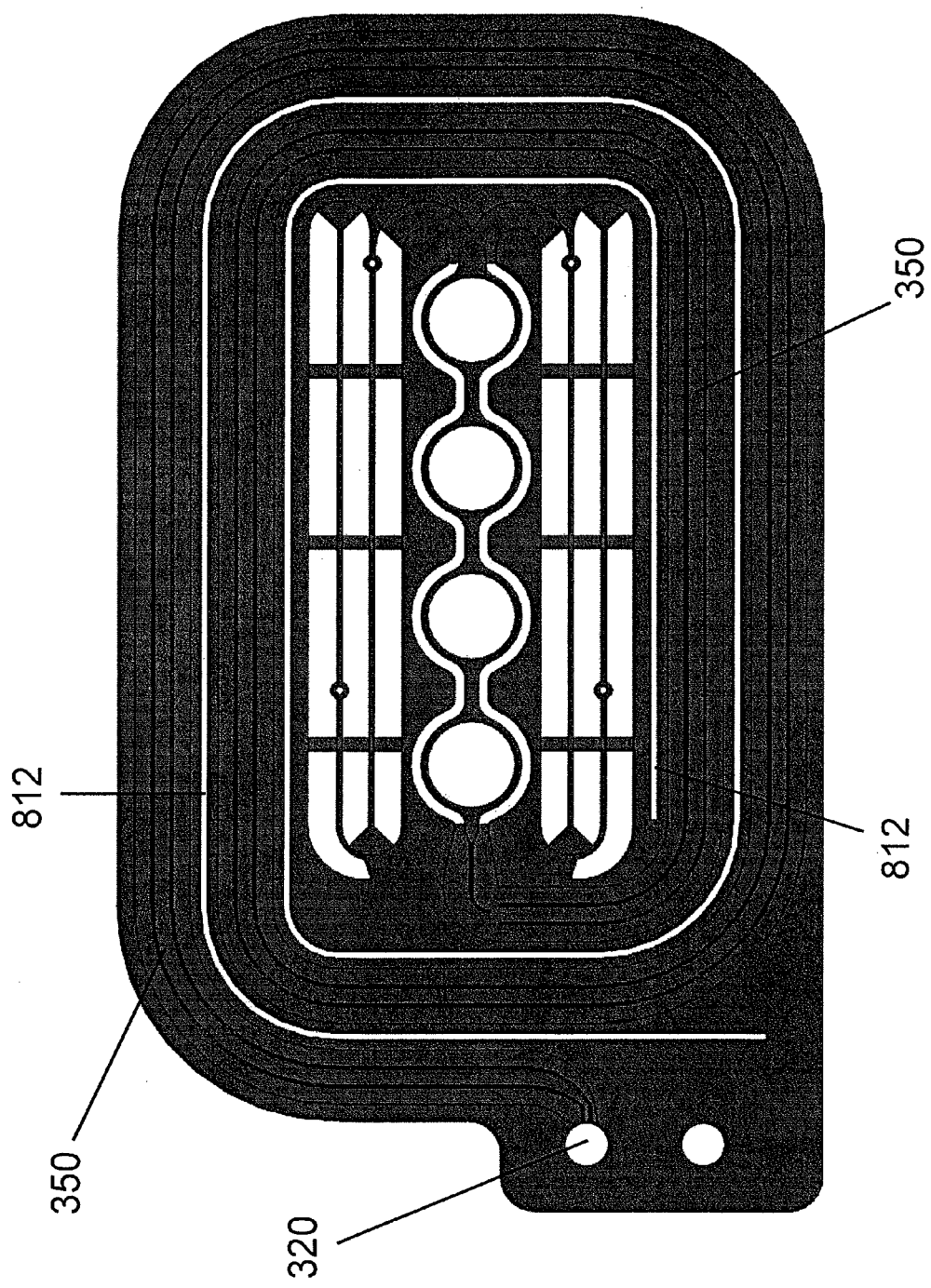
FIG. 12 shows an embodiment of a lamina having coiled fluid flow paths around a heat exchange region.

The channels can have any of a variety of shapes configured to surround a portion of or the entire flow pathway. For example, in the embodiment shown in FIG. 10, each channel 812 is formed by three straight segments that collectively form a substantial "U" shape around three sides of the flow paths. The segments need not be straight but could also be curved. In another embodiment, a plurality of channels 812 is used wherein each individual channel surrounds just a portion of the flow field and the plurality of channels collectively surrounds a majority of the flow paths. FIG. 11 shows another embodiment of the lamina that includes a pair of heat exchange regions 350 that are fed fluid from an inlet 320. The lamina may include two or more heat exchange regions 350 that are collectively or individually surrounded by channels 812 that serve to insulate the heat exchange regions. In yet another embodiment, shown in FIG. 12, the heat exchange regions 350 have a coiled configuration and is surrounded by a similarly coiled channel 812. The channel 812 serve to insulate the heat exchange regions 350.

Any of the fluid volumes or pathways within the stack 805 can be surrounded by one or more of the channels 812. In some embodiments, at least the heat exchange region 350 is substantially surrounded by one or more of the channels 812. In another embodiment, at least the heater region 355 is substantially surrounded by one or more of the channels 812. Or at least the residence chamber 360 is substantially surrounded by one or more of the channels 812. In other embodiments, the heat exchange region 350, the heater region 355 and the residence chamber 360 are substantially surrounded by one or more of the channels 812. The channels 812 can be filled with a material or can be empty. In the assembled stack of lamina, the channels are enclosed along the sides by the laminae themselves and enclosed on the top and bottom by one or more plates such that the channels collectively form an enclosed chamber that at least partially surrounds the fluid pathways of the laminae. Upon use of the system, pressure differentials within the system may cause air or any other fluid to evacuate from the channels 812 such that a vacuum or partial vacuum is formed. The vacuum acts to insulate the flow pathways from the outside environment preventing or inhibiting heat loss and ultimately reducing power consumption of the system.

C. Dialysate Preparation Sub-System

Figure 4:
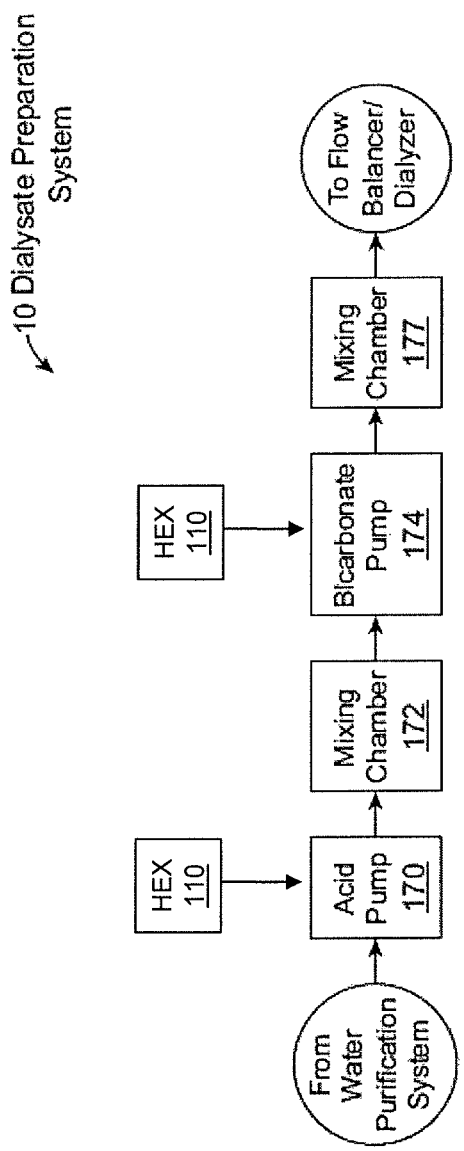
FIG. 4 shows a high level, schematic view of an implementation of a dialysate preparation system of the dialysis system.

The water is in a pasteurized state as it exits the water purification system 5 and flows into the dialysate preparation system 10. The dialysate preparation system 10 is configured to mix the pasteurized water with a supply of concentrate solutions in order to make dialysate. FIG. 4 shows a high level, schematic view of the dialysate preparation system 5. The embodiment of FIG. 4 is exemplary and it should be appreciated that variations are within the scope of this disclosure.

The dialysate preparation system 10 can include an acid pump 170 that fluidly communicates with a supply of concentrated acidified dialysate concentrate for mixing with the purified water. The water can flow from the water purification system 5 to the acid pump 170, which pumps the acid concentrate into the water. The water (mixed with acid) can then flow into a first mixing chamber 172, which is configured to mix the water with the acid such as by causing turbulent flow. From the first mixing chamber 172, the acid-water mixture can flow toward a bicarbonate pump 174. A sensor, such as a conductivity sensor, may be positioned downstream of the first mixing chamber 172. The conductivity sensor is configured to detect a level of electrolytes in the mixture. The conductivity sensor may be in a closed loop communication with the acid pump 170 and a control system that may regulate the speed of the acid pump to achieve a desired level of acid pumping into the water.

The bicarbonate pump 174 can pump bicarbonate concentrate into the acid-water mixture at a level sufficient to form dialysate. The resulting mixture of fluid flows into a second mixing chamber 177 and exits the second mixing chamber 177 as dialysate. Another sensor, such as a conductivity sensor, may be positioned downstream of the second mixing chamber 172. The second conductivity sensor may be in a closed loop communication with the bicarbonate pump 177. The dialysate can then flow toward the flow balancer system and the dialyzer.

D. Dialyzer Sub-System

Figure 5:
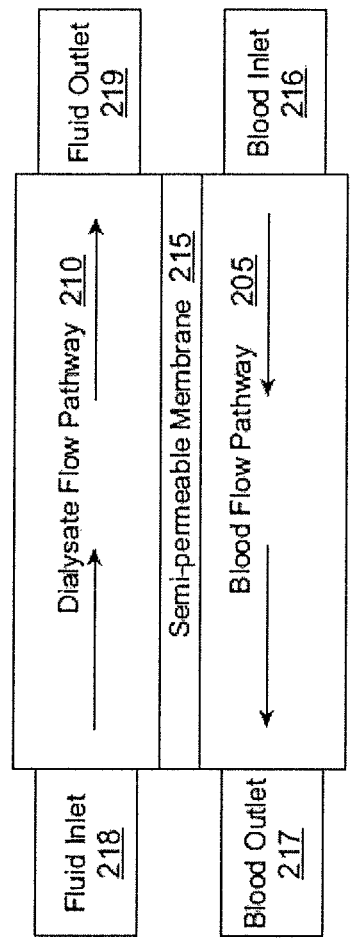
FIG. 5 is a schematic, cross-sectional view of an implementation of a dialyzer of the dialysis system.

FIG. 5 is a schematic, cross-sectional view of the dialyzer 15, which defines a blood compartment having a blood flow pathway 205 and a dialysate compartment having a dialysate flow pathway 210 separated by a transfer layer comprised of a semi-permeable membrane 215. In an embodiment, the dialyzer includes one or more microfluidic pathways such as micro flow fields and/or microchannels. Exemplary embodiments of dialyzers that utilize micro flow fields and/or microchannels and/or flow field dialyzers are described in U.S. Patent Publication No. 2010/0326914, filed Jun. 7, 2010, which is incorporated by reference in its entirety. However, the dialysis system can be used with any of a variety of dialyzers including a variety of commercially-available dialyzers.

The blood (from a patient) can enter the blood flow pathway 205 via a blood inlet 216, flow through the blood flow pathway 205, and exit via a blood outlet 217. The dialysate can enter the dialysate flow pathway 210 via a fluid inlet 218, flow through the dialysate flow pathway 210, and exit via a fluid outlet 219. The semi-permeable membrane 215 is configured to allow the transfer of one or more substances from the blood in the blood flow pathway 205 to the dialysate in the dialysate flow pathway 210, or visa-versa.

Some examples of materials that may be used as the semi-permeable membrane 215 include polymers, copolymers, metals, ceramics, composites, and/or liquid membranes. One example of a composite membrane is polysulfone-nanocrystalline cellulose composite membrane such as AN69 flat sheet membranes available from Gambro Medical. Gas-liquid contactor membranes may also be employed for transferring a substance between a liquid and gas such as for oxygenation of blood, whereby the membrane allows transfer of carbon dioxide and oxygen, such that oxygen transfers to blood from oxygen or oxygen-enriched air, and carbon dioxide transfers from the blood to the gas. Fluid membranes may also be employed. Fluid membranes can include a lamina having through cut microchannels containing fluid and a first and second membrane support positioned to contain fluid in the microchannels.

When flowing through the dialyzer 15, the blood and the dialysate may flow in a counter-flow configuration wherein blood flows through the blood flow pathway 205 in one direction and the dialysate flows through the dialysate flow pathway 210 in the opposite direction. The dialyzer 15 is described in the context of having a counter-flow configuration although a cross-flow configuration may also be used. As the blood and water flow along the membrane 215, hemodialysis can occur. The dialyzer 15 is also configured to perform ultrafiltration wherein a pressure differential across the membrane 215 results in fluid and dissolved solutes passing across the membrane 215 from the blood to the dialysate.

The dialyzer 15 is also configured to perform hemodiafiltration wherein solute movement across the semipermeable membrane 215 is governed by convection rather than by diffusion. A positive hydrostatic pressure differential between the blood flow pathway 205 and the dialysate flow pathway 210 drives water and solutes across the semipermeable membrane 215 from the blood flow pathway to the fluid flow pathway. Solutes of both small and large molecules get dragged through the semipermeable membrane 215 along with the fluid. In a typical hemodiafiltration procedure, the direction of water and solute movement can oscillate between moving water and solutes from the blood into the dialysate and moving water and solutes from the dialysate into the blood. Over a predetermined span of time, there is a net zero loss and zero net gain of fluid from the blood into the dialysate. However, during discrete time periods within that span of time, there can be a net loss of fluid from the blood into the dialysate and a net gain of fluid into the blood from the dialysate.

E. Flow Balancer System

Figure 6:
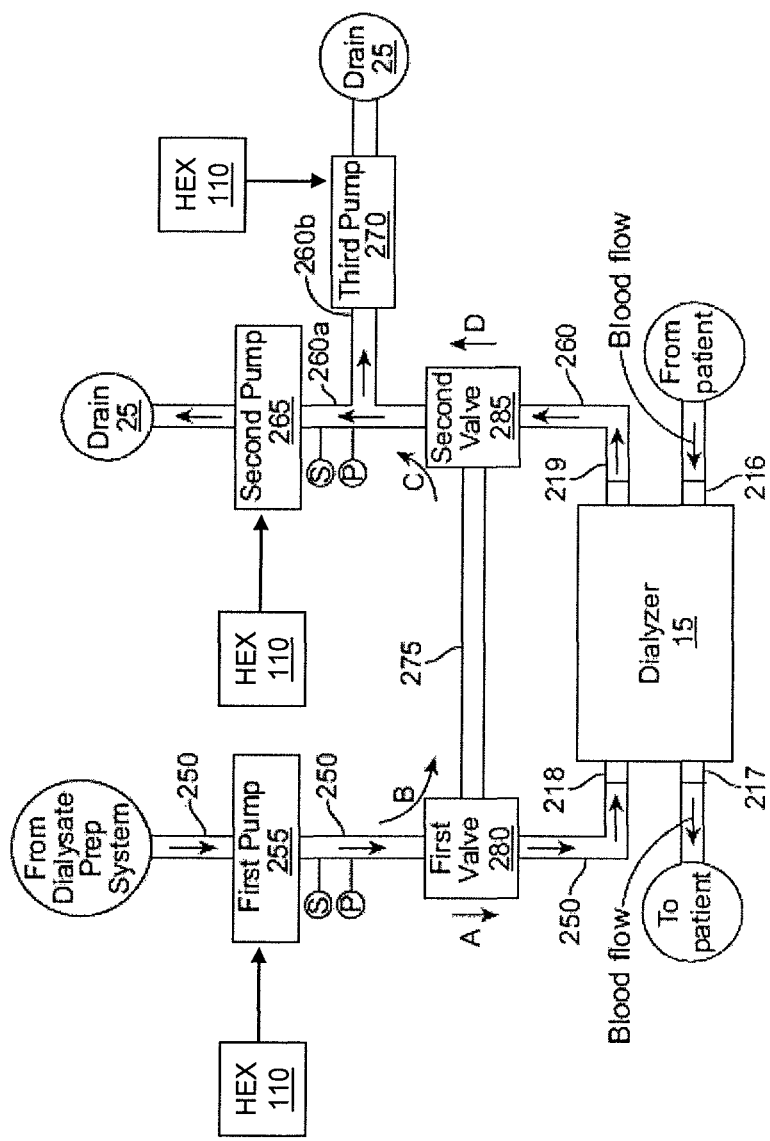
FIG. 6 shows a schematic view of an implementation of a flow balance system.

FIG. 6 shows a schematic view of the flow balancer system 20 including the dialyzer 15. The flow balancer system 20 is adapted to regulate the flow of dialysate into and out of the dialyzer 15 to achieve various types of dialysis, including hemodialysis, ultrafiltration, and hemodiafiltration. The flow balancer system 20 can include a first pump for pumping dialysate into a dialyzer and a second pump for pumping dialysate out of the dialyzer. The system can also include a third pump that provides improved control of a level of ultrafiltration, hemodiafiltration, or both. By varying the relative pump speeds of the pumps, an operator can vary the level of blood filtration and can also selectively achieve ultrafiltration and hemodiafiltration of the blood.

The flow balancer system 20 can include plumbing that forms a plurality of fluid flow pathways, which may be any type of conduit through which a fluid such as dialysate may flow. The fluid flow pathways can include an inlet pathway 250 through which a fluid such as unused dialysate flows from the dialysate preparation system 10 toward and into the dialyzer 15. At least a first pump 255 is positioned along or in communication with the inlet pathway 250 for pumping the fluid toward the dialyzer 15 at a desired flow rate. One or more sensors S may be coupled to the fluid flow pathway for sensing one or more characteristics of the incoming fluid, such as pressure, flow rate, temperature, conductivity, etc. In addition, one or more sample ports P may be coupled to the fluid flow pathways that provide access to fluid flowing through the piping. FIG. 6 shows the sensors S and sample ports P coupled to the fluid flow pathways at specific locations, although the quantity and locations of the sensors S and sample ports P may vary.

The fluid flow pathways can further include an outlet pathway 260 through which used dialysate flows out of the dialyzer 15 toward one or more drains 25. In some embodiments, the dialysate exiting the dialyzer may be used to pre-heat other incoming fluids in the system, such as the water stream entering the heat exchange and purification system, before reaching the drain 25. The outlet pathway 260 can bifurcate into two or more outlet pathways including a main outlet pathway 260a and a secondary outlet pathway 260b. At least a second pump 265 can be positioned along or in communication with the main outlet pathway 260a for pumping the dialysate out of and away from the dialyzer 15 through the main outlet pathway 260a.

A third pump 270 can be positioned along or in communication with the secondary outlet pathway second valve 285. The third pump 270 can be used to augment fluid flow through the fluid flow pathways such as to selectively achieve differentials in flow rates between the inlet pathway 250 and the outlet pathway 260 pursuant to achieving various types of dialysis, including hemodialysis, ultrafiltration, and hemodiafiltration, as described more fully below. The third pump can pump dialysate through the fluid flow pathways when the system is in dialysis mode. The third pump may also pump another fluid, such as water or disinfectant, when the system is in a different mode, such as in a calibration mode or in a cleaning mode.

The third pump 270 can be positioned along the inlet pathway 250 upstream of the inlet 218 of the dialyzer 15. In this embodiment, the secondary outlet pathway 260 branches off the inlet pathway 250 at a location downstream of the first pump 255 and upstream of the first valve 280. The third pump 270 can pump fluid toward the drain 25. In another embodiment, the third pump 270 and the second pump 265 are both positioned along a single, non-bifurcating outflow pathway.

Various types of pumps may be used for the first, second and third pumps. In an embodiment, the pumps are nutating pumps. On other embodiments, the pumps could be rotary lobe pumps, progressing cavity pumps, rotary gear pumps, piston pumps, diaphragm pumps, screw pumps, gear pumps, hydraulic pumps, vane pumps, regenerative (peripheral)

pumps, or peristaltic pumps, or any combination thereof. Other types of pumps can also be used. The first pump 255 and the second pump 265 may be driven by a common shaft to ensure synchrony of the pump strokes and the volume of fluid pumped. It is understood that first pump 255 and the second pump 265 may also be fully independent from each other.

As mentioned, any of a variety of fluid conduits may be used to form the fluid flow pathways of the flow balancer system 20. In an embodiment, at least a portion of the fluid flow pathway is formed of piping having an inside diameter from ⅛ inch to ½ inch. The flow rate in the piping could range between about 50 ml/min to about 1,000 ml/min. In an embodiment, the flow rate is in the range of between about 100 ml/min and about 300 ml/min.

The fluid flow pathways further can include a bypass pathway 275 that directly connects fluidly the inlet pathway 250 and the outlet pathway 260. An exemplary purpose of the bypass pathway 275 is to provide a fluid flow pathway where fluid can flow into and out of the dialysis system and bypass the dialyzer 15, such as for flushing, cleaning or calibrating the system. In an embodiment, the junction between the inlet pathway 250 and bypass pathway 275 is located upstream of the fluid inlet 120 of the dialyzer 15, and the junction between the bypass pathway 275 and the outlet pathway is located downstream of the fluid outlet 125 of the dialyzer 15. However, other configurations of the bypass pathway 275 can be used to achieve bypassing of the dialyzer 15.

A first valve 280 can be positioned at the junction between the inlet pathway 250 and the bypass pathway 275. A second valve 285 can be positioned at the junction between the bypass pathway 275 and the outlet pathway 260. The first valve 280 and second valve 285 can be three-way valves, such as solenoid valves, that can be used to selectively regulate fluid flow through the fluid flow pathways. That is, the first valve 280 can be set to either of two or more settings including (1) a dialysis setting wherein the first valve directs all incoming fluid along the inlet pathway 250 toward the dialyzer 15 (as represented by arrow A in FIG. 6) and prevents incoming fluid from flowing into the bypass pathway 275; or (2) a bypass setting wherein the first valve 280 diverts all the incoming fluid into the bypass pathway 275 (as represented by arrow B in FIG. 6) and the prevents incoming fluid from flowing past the first valve toward the dialyzer 15.

The second valve 285 can also be set to either of two settings including (1) a bypass setting wherein the second valve 285 directs incoming fluid from the bypass pathway 275 into the outlet pathway 260 (as represented by arrow C in FIG. 6); or (2) a dialysis setting wherein the second valve 285 closes flow from the bypass pathway 275 such that outgoing fluid from the dialyzer outlet 125 continues to flow outward along the outlet pathway 260 (as represented by arrow D in FIG. 6.) The first valve 280 and the second valve 285 are generally both set in tandem to either the bypass setting or the dialysis setting. The system may include a control and safety system that ensures that the first and second valves are not set to incompatible settings.

The arrangement of the various components of the dialysis system shown in FIG. 6 is exemplary and other arrangements are possible. For example, the flow pathways and the pumps may be placed in different locations along the flow pathways from what is shown in FIG. 6. In an embodiment, the third pump 270 can be positioned in the flow pathway at a location upstream of the dialyzer 15 and downstream of the first valve 280 or the third pump can be positioned downstream of the dialyzer 15 and upstream of the second valve 285. Moreover, the system can employ more than three pumps.

Purified water from within the systems described herein can be used to flush, prime and lubricate components of the various pumps of the various sub-systems. For example, purified water from the heat exchanger system 110 can be used to prime or flush the pump gland, pump heads and seals of the acid pump 170 and/or the bicarbonate pump 174 of the dialysate preparation system 10 (FIG. 4). Similarly, purified water from the heat exchanger system 110 can be used to prime the one or more of the flow balancer pumps 255, 265, 270 (FIG. 6). Using purified water internal to the system as pump gland flush fluid to lubricate heads of flow system reduces the need for fluid from an outside source and reduces the overall water consumption of the systems and takes advantage of the highly pure water available from the HEX system. In this regard, the plumbing of the system may include one or more flow pathway that are dedicated to guiding purified water to the pump or pumps that are to be flushed. The control system may be configured to automatically guide purified water to the pumps or the control system may be configured to permit a user to selectively guide purified water to the pumps.

F. Other Applications

As mentioned above, the fluid purification systems described herein can be useful for purposes other than dialysis. For example, the water purification sub-system 5 and in particular, the heat exchanger system 110 can be beneficial for purification of fluids such as water sources for human consumption. Further, the fluid purification systems described herein need not be powered by conventional energy sources such as by plugging into an electrical outlet. The fluid purification systems described herein can be powered by renewable energy sources including solar, user-powered generator, or other gridless energy sources. Such power sources allow the system to be used in emergency situations, power failures, remote locations or any other off-grid application such as in poor regions of the world where electricity is not readily available and clean water may be in high demand. In some embodiments, the heat exchanger system 110 can be coupled to a user-powered generator and include one or more batteries configured to run small appliances and capable of being charged by the generator. The user-powered generator can be cranked such as by hand or by pedaling on a bicycle to charge the batteries and power the heat exchanger system 110.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

TABLE 1

| Temperature | Time | Pasteurization Type |
|---|---|---|
| 63° C. (145° F.) | 30 minutes | Vat Pasteurization |
| 72° C. (161° F.) | 15 seconds | High Temperature Short Time Pasteurization (HTST) |
| 89° C. (191° F.) | 1.0 second | Higher-Heat Shorter Time Pasteurization (HHST) |
| 90° C. (194° F.) | 0.5 second | Higher-Heat Shorter Time Pasteurization (HHST) |
| 94° C. (201° F.) | 0.1 second | Higher-Heat Shorter Time Pasteurization (HHST) |
| 96° C. (204° F.) | 0.05 second | Higher-Heat Shorter Time Pasteurization (HHST) |
| 100° C. (212° F.) | 0.01 second | Higher-Heat Shorter Time Pasteurization (HHST) |
| 138° C. (280° F.) | 2.0 seconds | Ultra High Temperature Pasteurization (UHT) |

What is claimed is:

1. A water treatment device, comprising:
at least first and second laminae arranged in a stacked relationship so as to form a stack of laminae, each lamina having a fluid flow field;
an inlet pathway comprising the fluid flow field of the first lamina, the inlet pathway having a heat exchange region;
an outlet pathway comprising the fluid flow field of the second lamina, the outlet pathway having a heat exchange region;
a metal transfer layer disposed between the heat exchange region of the inlet pathway and the heat exchange region of the outlet pathway, the metal transfer layer being configured to transfer heat between fluid flowing in the inlet pathway and fluid flowing in the outlet pathway;
a first cut-out in the first lamina, wherein the first cut-out is separate from and surrounds at least a portion of the fluid flow field of the first lamina without intersecting the first lamina fluid flow field;
a second cut-out in the second lamina, wherein the second cut-out is separate from and surrounds at least a portion of the fluid flow field of the second lamina without intersecting the second lamina fluid flow field, and wherein the first and second cut-outs vertically align with one another in the stack to form a collective cut-out that extends through the stack; and
a first plate on the top of the stack and a second plate on the bottom of the stack, wherein the first and second plates enclose the top and bottom of the collective cut-out creating an insulating chamber to the fluid flow fields of the stack.

2. The device of claim 1, wherein each of the first and second cut-outs surrounds a respective flow field along at least three sides of the flow field.

3. The device of claim 1, wherein each of the first and second cut-outs surrounds at least eighty percent of its respective flow field.

4. The device of claim 1, wherein the stack includes more than two laminae.

5. The device of claim 1, wherein a partial vacuum is formed within the insulating chamber.

* * * * *